(12) United States Patent
Shamir et al.

(10) Patent No.: US 12,343,529 B2
(45) Date of Patent: Jul. 1, 2025

(54) METHODS, SYSTEMS, AND APPARATUSES FOR GUIDING TRANSDUCER PLACEMENTS FOR TUMOR TREATING FIELDS

(71) Applicant: Novocure GmbH, Root D4 (CH)

(72) Inventors: Reuven Ruby Shamir, Haifa (IL); Noa Urman, Haifa (IL); Zeev Bomzon, Haifa (IL); Oren Ben Zion Bakalo, Haifa (IL); Yana Glozman, Haifa (IL)

(73) Assignee: Novocure GmbH, Baar (CH)

( * ) Notice: Subject to any disclaimer, the term of this patent is extended or adjusted under 35 U.S.C. 154(b) by 0 days.

(21) Appl. No.: 17/210,339

(22) Filed: Mar. 23, 2021

(65) Prior Publication Data

US 2021/0299439 A1   Sep. 30, 2021

Related U.S. Application Data

(60) Provisional application No. 63/056,262, filed on Jul. 24, 2020, provisional application No. 63/002,937, filed on Mar. 31, 2020.

(51) Int. Cl.
*A61N 1/36* (2006.01)
*G06T 5/50* (2006.01)
(Continued)

(52) U.S. Cl.
CPC ............ *A61N 1/36002* (2017.08); *G06T 5/50* (2013.01); *G06T 7/0012* (2013.01); *G06T 7/30* (2017.01);
(Continued)

(58) Field of Classification Search
None
See application file for complete search history.

(56) References Cited

U.S. PATENT DOCUMENTS 7,565,205 B2   7/2009  Palti
2009/0290771 A1* 11/2009  Frank ..................... A61B 6/463
                                        382/128
(Continued)

FOREIGN PATENT DOCUMENTS

CN        109009204 A     12/2018
JP        2013-534167 A    9/2013
(Continued)

OTHER PUBLICATIONS

Chaudhry et al. (100A System (Tumor Treating Fields) transducer array layout planning for glioblastoma: a NovoTAL™ system user study, World Journal of Surgical Oncology, 2015) (Year: 2015).*
(Continued)

*Primary Examiner* — Kyle Zhai
(74) *Attorney, Agent, or Firm* — McCarter & English, LLP; Michael A. Sartori

(57) ABSTRACT

A method of assisting transducer placements on a subject's body for applying tumor treating fields includes: determining, based on one or more images associated with a portion of a subject's body, a first image data, wherein the first image data comprises one or more recommended transducer placement positions; determining, based on the one or more images, a second image data, wherein the second image data comprises one or more transducer placement positions; registering the second image data to the first image data; and generating a composite data comprising the one or more transducer placement positions and the one or more recommended transducer array placement positions.

19 Claims, 24 Drawing Sheets

(51) Int. Cl.
| | |
|---|---|
| G06T 7/00 | (2017.01) |
| G06T 7/30 | (2017.01) |
| G06T 7/70 | (2017.01) |
| G06T 17/00 | (2006.01) |
| G16H 20/40 | (2018.01) |
| G16H 30/40 | (2018.01) |
| G16H 40/67 | (2018.01) |
| G16H 50/50 | (2018.01) |

(52) U.S. Cl.
CPC .............. *G06T 7/70* (2017.01); *G06T 17/00* (2013.01); *G16H 20/40* (2018.01); *G16H 30/40* (2018.01); *G16H 40/67* (2018.01); *G16H 50/50* (2018.01); *G06T 2207/20221* (2013.01); *G06T 2207/30096* (2013.01)

(56) References Cited

U.S. PATENT DOCUMENTS

| | | | |
|---|---|---|---|
| 2011/0268333 A1* | 11/2011 | Klingenbeck | A61B 6/507 382/131 |
| 2013/0289679 A1 | 10/2013 | Eckhouse et al. | |
| 2017/0120041 A1 | 5/2017 | Wenger et al. | |
| 2017/0143263 A1* | 5/2017 | Soma | A61B 5/291 |
| 2018/0160933 A1 | 6/2018 | Urman et al. | |
| 2019/0059732 A1 | 2/2019 | Kim et al. | |
| 2019/0117956 A1 | 4/2019 | Wenger et al. | |
| 2019/0314631 A1 | 10/2019 | Wong et al. | |
| 2020/0163647 A1* | 5/2020 | Hakkens | A61B 8/4236 |
| 2020/0337789 A1* | 10/2020 | Meglan | G09B 23/285 |
| 2021/0209847 A1* | 7/2021 | Yau | B29C 64/393 |

FOREIGN PATENT DOCUMENTS

| | | |
|---|---|---|
| JP | 2014-61093 A | 4/2014 |
| JP | 2018-537136 A | 12/2018 |
| JP | 2020-501689 A | 1/2020 |
| TW | 201940205 A | 10/2019 |
| WO | WO-2019036332 A1 | 2/2019 |
| WO | WO-2019139935 A1 | 7/2019 |

OTHER PUBLICATIONS

Ballo et al., "Correlation of Tumor Treating Fields Dosimetry to Survival Outcomes in Newly Diagnosed Glioblastoma: A Large-Scale Numerical Simulation-Based Analysis of Data from the Phase 3 EF-14 Randomized Trial," International Journal of Radiation Oncology, Biology, Physics, 2019; 104(5), pp. 1106-1113.

Bomzon et al., "Using Computational Phantoms to Improve Delivery of Tumor Treating Fields (TTFIELDS) to Patients," IEEE, 2016, pp. 6461-6464.

NovoTTFTM-100A System (Tumor Treating Fileds) transducer array layout planning for glioblastoma: a NovoTALTM syste user study, World J Surg Oncol. Nov. 11, 2015; 13: 316. [Cited in Office Action in IL Application No. 294495, dated Dec. 31, 2024].

* cited by examiner

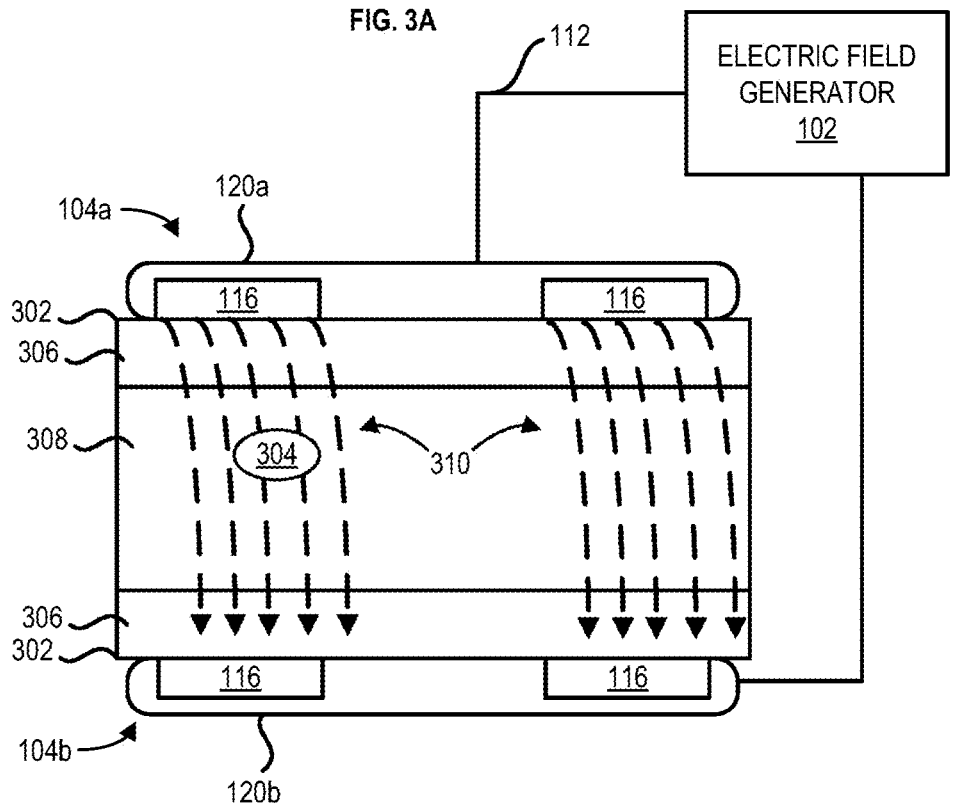
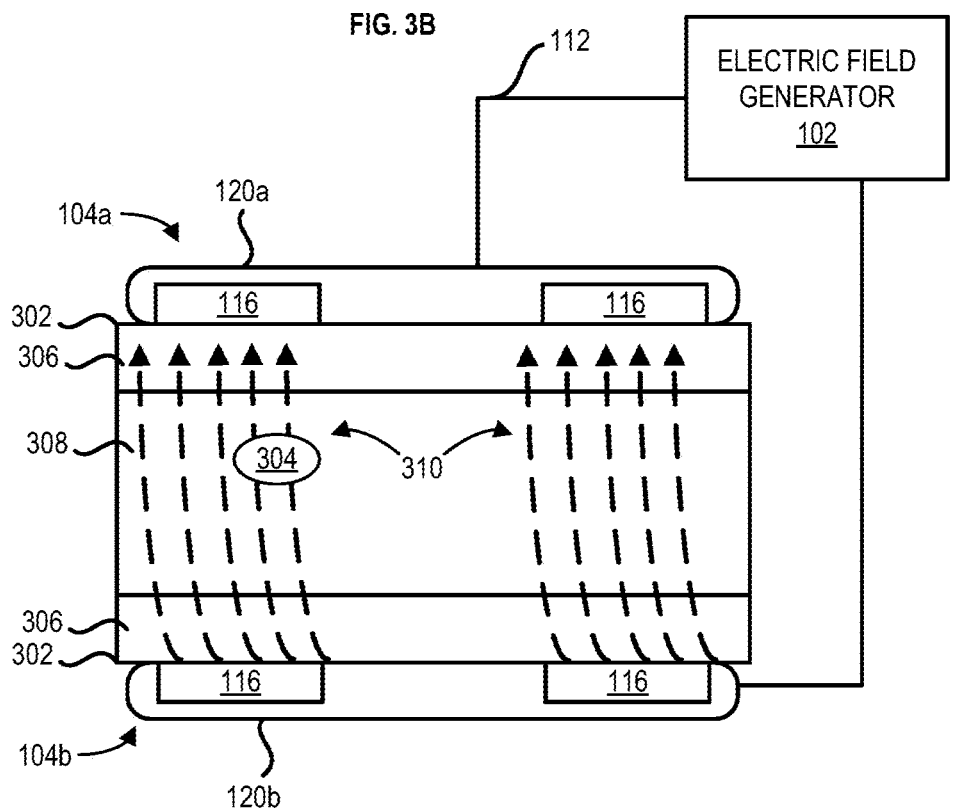

1432

TA 2:
Shift 2cm towards to the bottom and 1cm towards the face

FIG. 14C

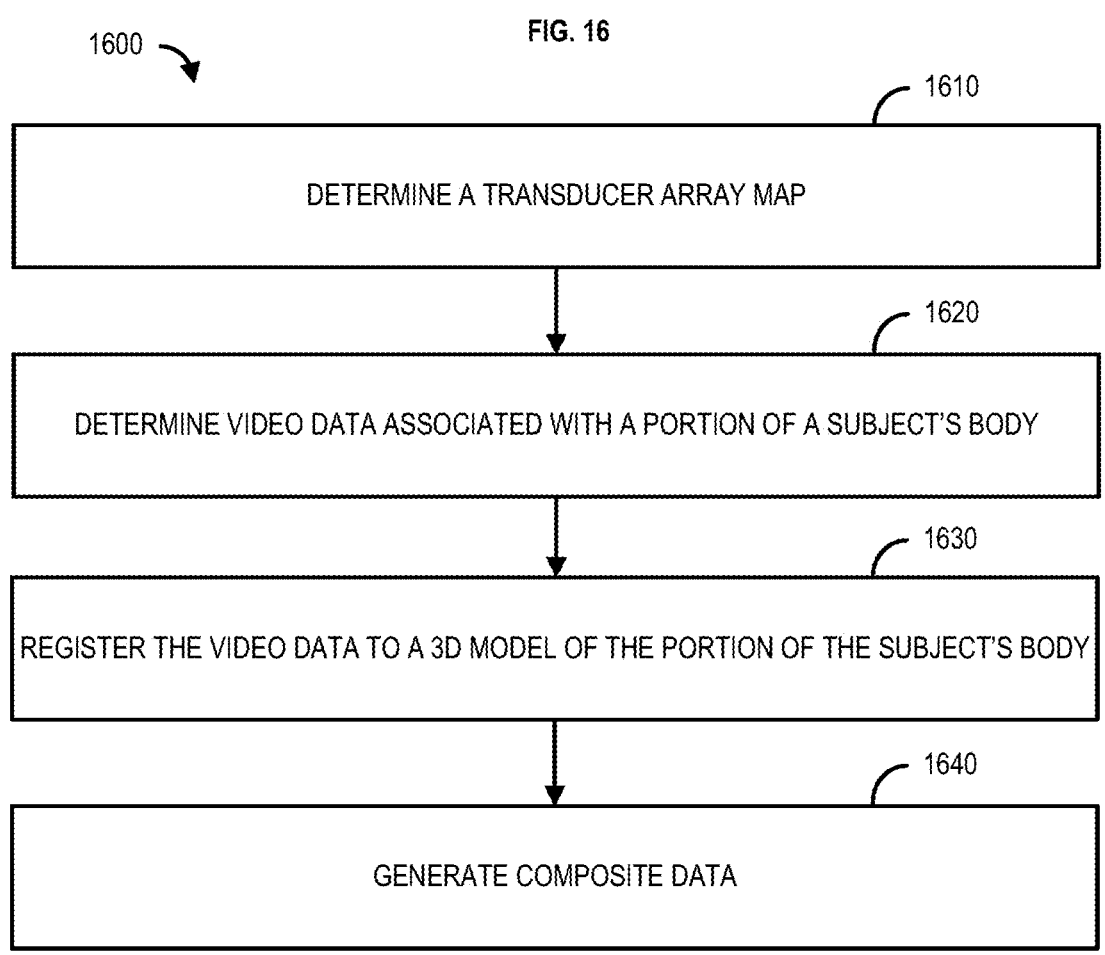

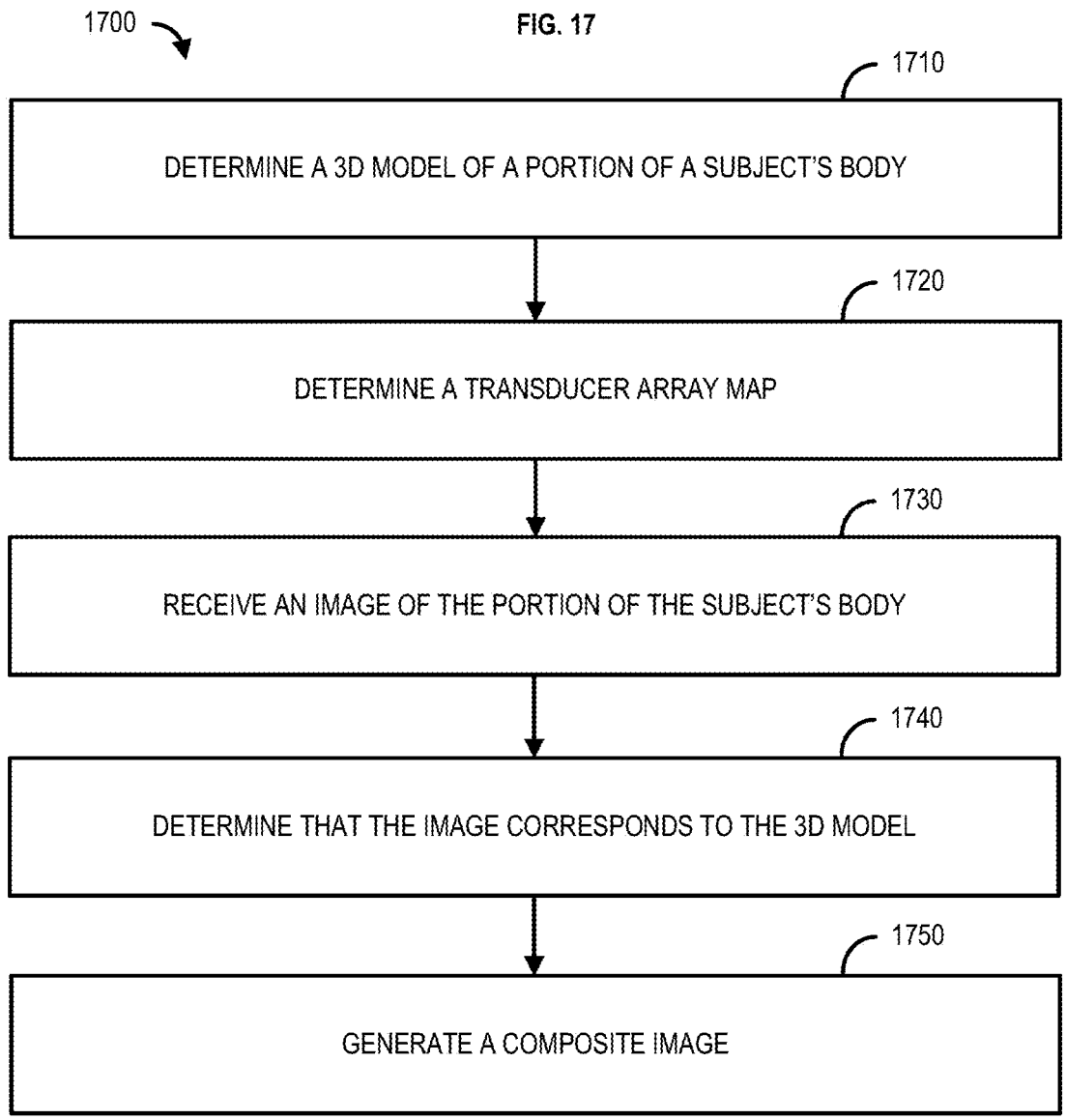

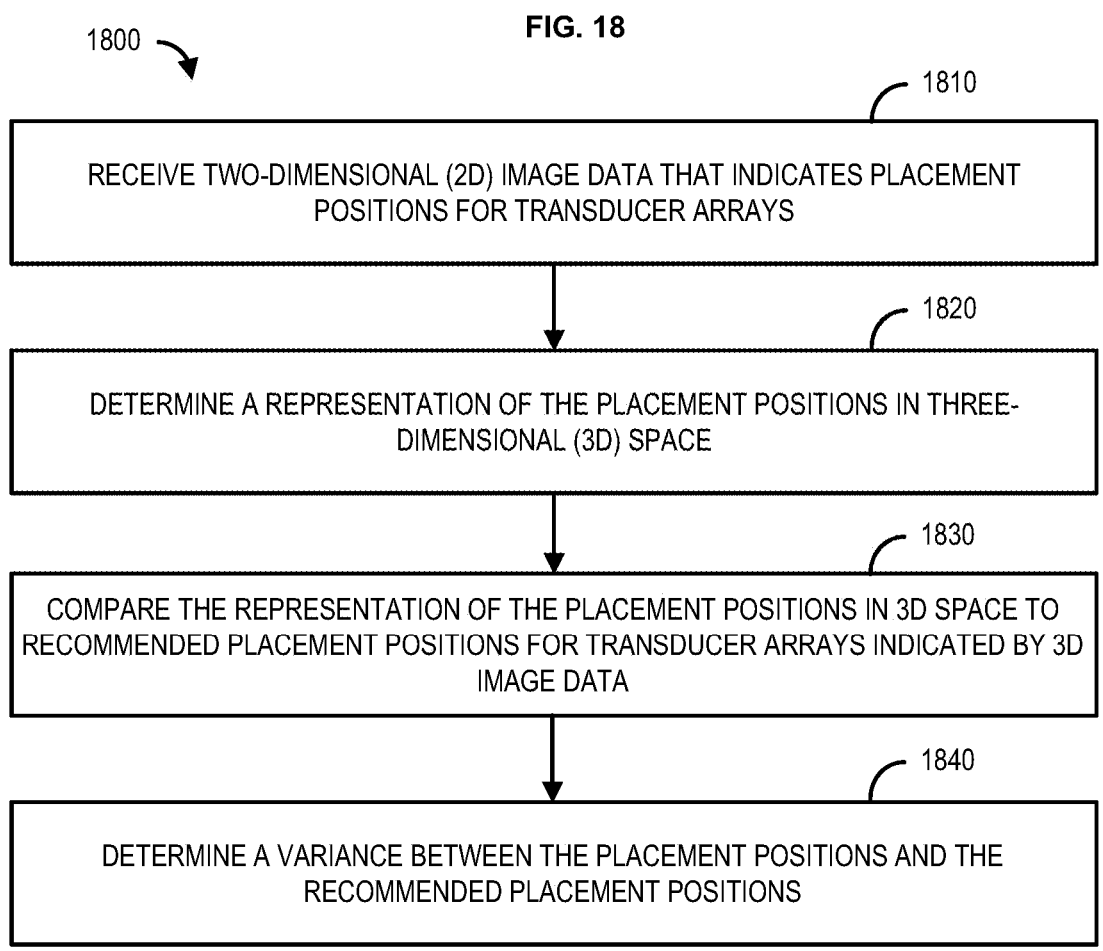

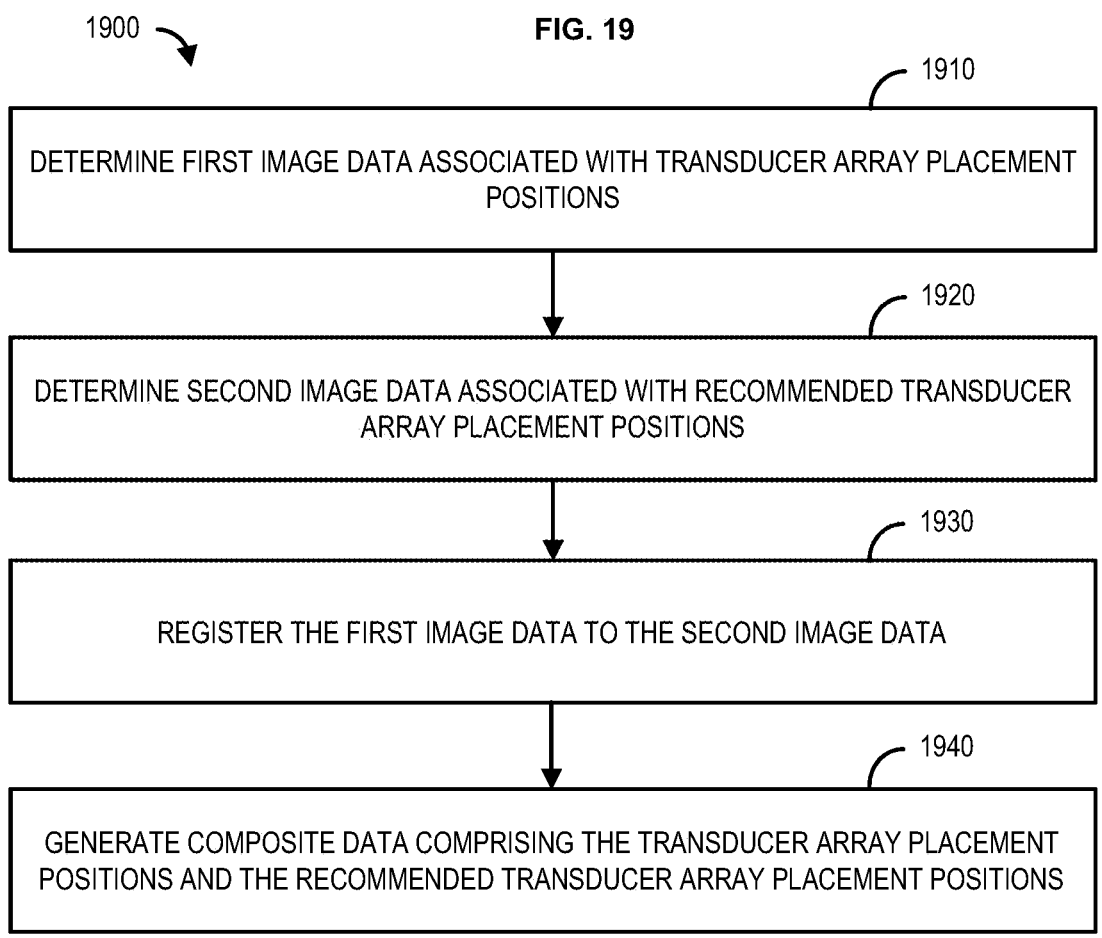

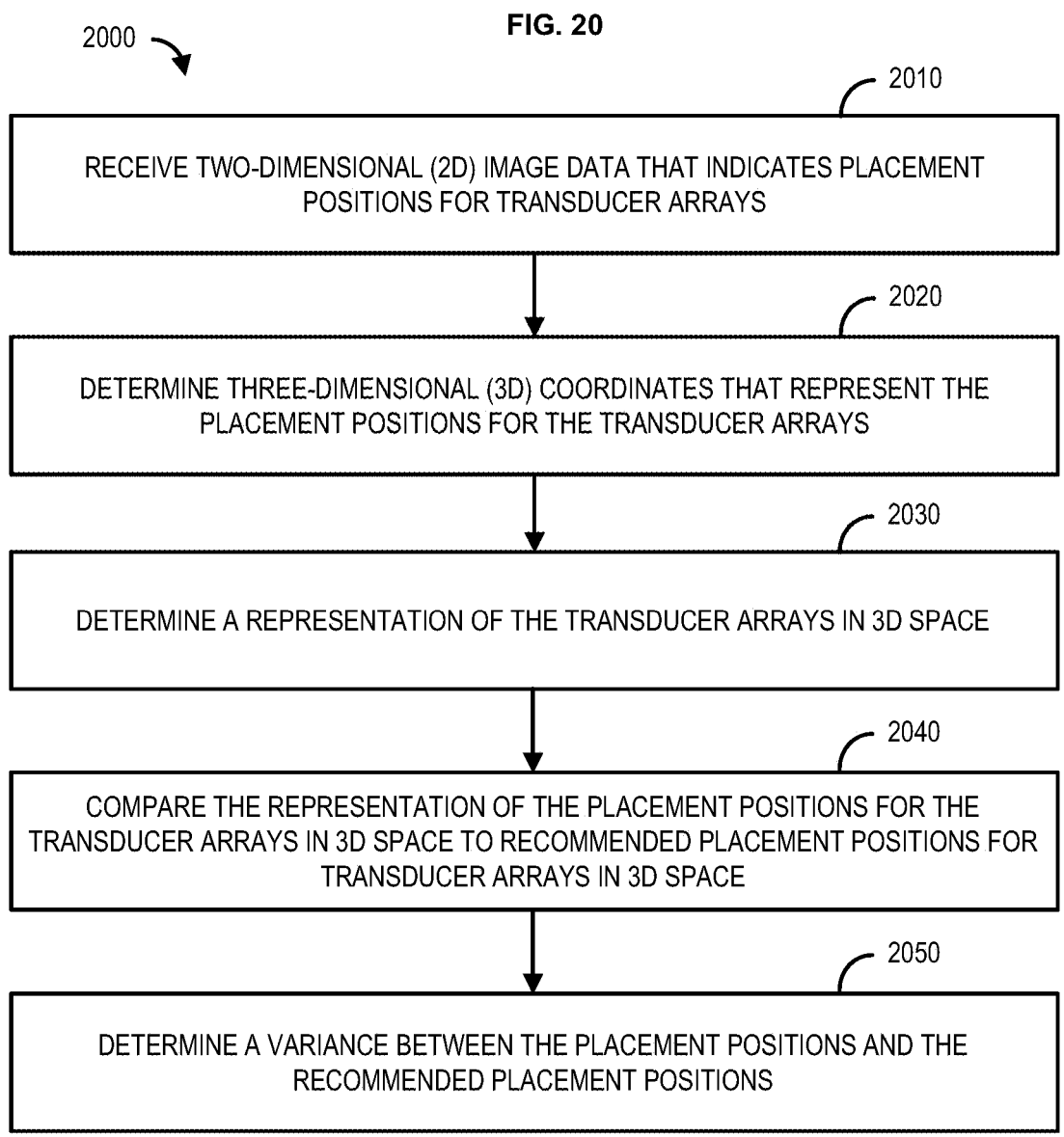

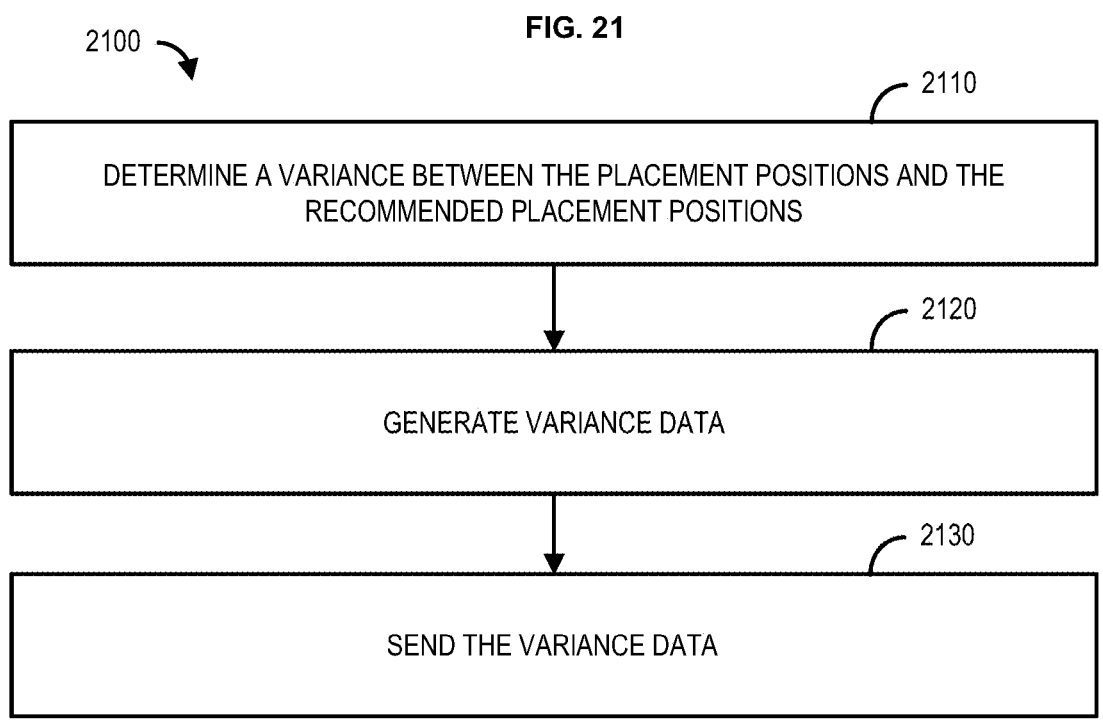

METHODS, SYSTEMS, AND APPARATUSES FOR GUIDING TRANSDUCER PLACEMENTS FOR TUMOR TREATING FIELDS

CROSS-REFERENCE TO RELATED APPLICATIONS

This application claims priority to U.S. Patent Application No. 63/002,937 filed Mar. 31, 2020 and U.S. Patent Application No. 63/056,262 filed Jul. 24, 2020, both of which are incorporated herein by reference.

BACKGROUND

Tumor Treating Fields, or TTFields, are low intensity (e.g., 1-3 V/cm) alternating electrical fields within the intermediate frequency range (100-300 kHz). This non-invasive treatment targets solid tumors and is described in U.S. Pat. No. 7,565,205. TTFields disrupt cell division through physical interactions with key molecules during mitosis. TTFields therapy is an approved mono-treatment for recurrent glioblastoma and an approved combination therapy with chemotherapy for newly diagnosed patients. These electrical fields are induced non-invasively by transducer arrays (i.e., arrays of electrodes) placed directly on the patient's scalp. TTFields also appear to be beneficial for treating tumors in other parts of the body.

Patient-specific optimized transducer placement may increase and/or improve electric field dosage to a target area, such as a tumor, to improve the efficacy of TTFields treatment. Ensuring that transducer arrays are placed properly on a patient is difficult due to minimal and/or no visibility of the target portion (e.g., head/scalp, torso, etc.) of the user's body. Misaligned and/or improperly placed TAs decreases the efficacy of TTFields treatment.

SUMMARY OF THE INVENTION

One aspect of the invention is directed to a method of assisting transducer placements on a subject's body for applying tumor treating fields. The method comprises: determining, based on one or more images associated with a portion of a subject's body, a first image data, wherein the first image data comprises one or more transducer placement positions; determining, based on the one or more images, a second image data, wherein the second image data comprises one or more recommended transducer placement positions; registering the first image data to the second image data; and generating a composite data comprising the one or more transducer placement positions and the one or more recommended transducer array placement positions.

Another aspect of the invention is directed to another method of assisting transducer placements on a subject's body for applying tumor treating fields. The method comprises: generating, based on a first image data, a three-dimensional (3D) model of a portion of the subject's body, wherein the 3D model comprising a presentation of one or more recommended transducer placement positions; receiving a second image data of the portion of the subject's body, determining, based on the second image data, a representation of the one or more placement positions for one or more transducers in a three-dimensional (3D) space; comparing the representation of the one or more placement positions for the one or more transducers in the 3D space to the presentation of the one or more recommended transducer placement positions in the 3D model; and determining and outputting, based on the comparison, a variance of at least one of the one or more placement positions for the one or more transducer from at least one of the one or more recommended transducer placement positions.

Another aspect of the invention is directed to an apparatus of assisting transducer placements on a subject's body for applying tumor treating fields. The apparatus comprises: one or more processors; and a memory storing processor executable instructions that, when executed by the one or more processors, cause the apparatus to: determine, based on one or more images associated with a portion of a subject's body, a first image data, wherein the first image data comprising one or more transducer placement positions; determine, based on the one or more images, a second image data, wherein the second image data comprising one or more recommended transducer placement positions; register the first image data to the second image data; and generate a composite data comprising the one or more transducer placement positions and the one or more recommended transducer placement positions.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 3A and FIG. 3B illustrate an example application of the apparatus for electrotherapeutic treatment.

FIGS. 14A-14C show examples of visual notification for guided transducer array placements for TTFields.

FIG. 16 is a flowchart depicting another example of guided transducer array placement for TTFields.

FIG. 17 is a flowchart depicting another example of guided transducer array placement.

FIG. 18 is a flowchart depicting another example of guided transducer array placement.

FIG. 19 is a flowchart depicting another example of guided transducer array placement.

FIG. 20 is a flowchart depicting another example of guided transducer array placement.

FIG. 21 is a flowchart depicting an example of generating variance data.

Various embodiments are described in detail below with reference to the accompanying drawings, wherein like reference numerals represent like elements.

DESCRIPTION OF EMBODIMENTS

Figure 1:
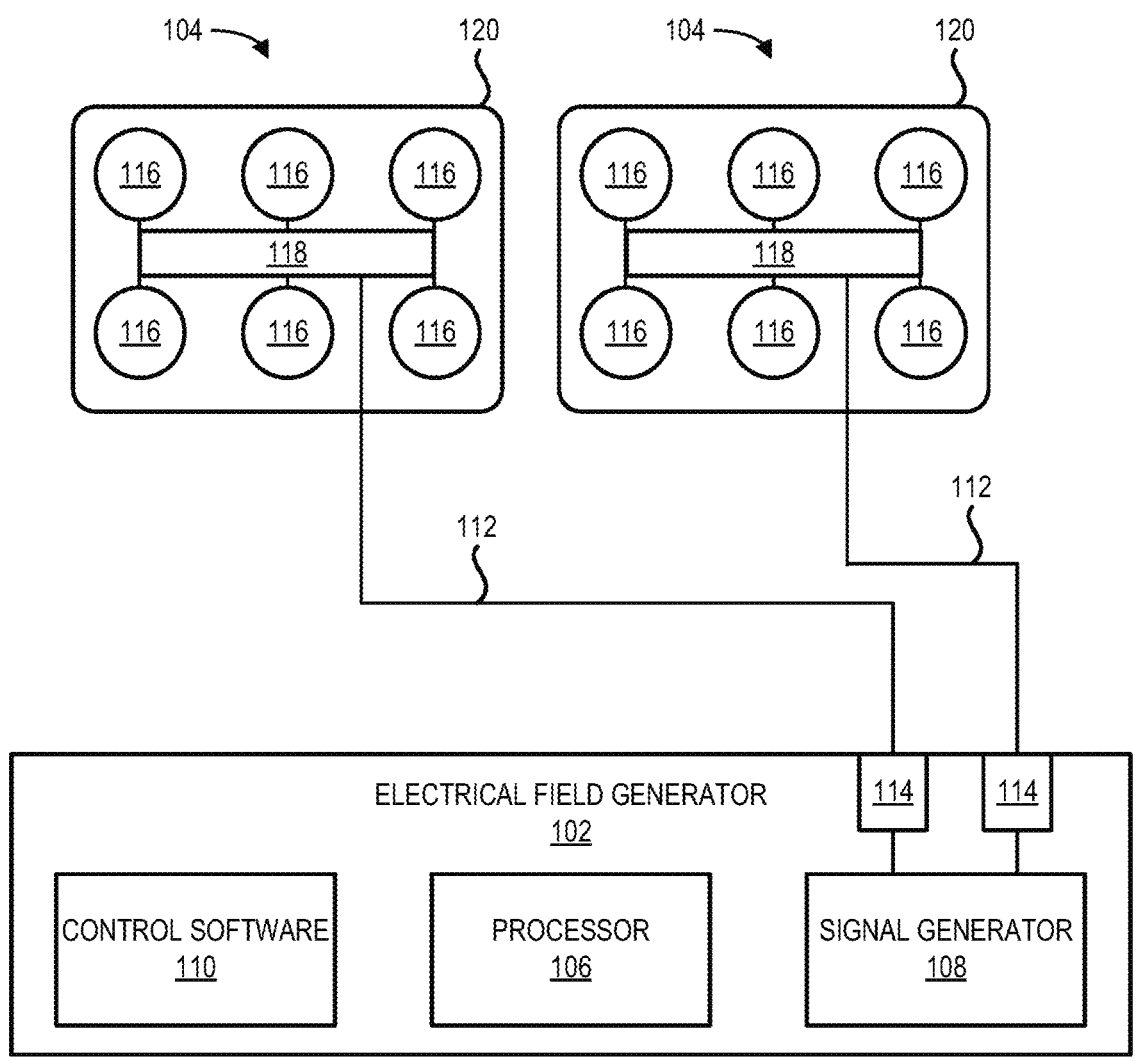
FIG. 1 shows an example apparatus for electrotherapeutic treatment.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that may be performed it is understood that each of these additional steps may be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, may be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that may direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, may be implemented by special purpose hardware-based computer systems that perform the specified functions or steps, or combinations of special purpose hardware and computer instructions.

TTFields, also referred to herein as alternating electrical fields, are established as an anti-mitotic cancer treatment modality because they interfere with proper micro-tubule assembly during metaphase and eventually destroy the cells during telophase and cytokinesis. The efficacy increases with increasing field strength and the optimal frequency is cancer cell line dependent with 200 kHz being the frequency for which inhibition of glioma cells growth caused by TTFields is highest. For cancer treatment, non-invasive devices were developed with capacitively coupled transducers that are placed directly at the skin region close to the tumor, for example, for patients with Glioblastoma Multiforme (GBM), the most common primary, malignant brain tumor in humans.

Because the effect of TTFields is directional with cells dividing parallel to the field affected more than cells dividing in other directions, and because cells divide in all directions, TTFields are typically delivered through two pairs of transducer arrays that generate perpendicular fields within the treated tumor. More specifically, one pair of transducer arrays may be located to the left and right (LR) of the tumor, and the other pair of transducer arrays may be located anterior and posterior (AP) to the tumor. Cycling the field between these two directions (i.e., LR and AP) ensures that a maximal range of cell orientations is targeted. Other positions of transducer arrays are contemplated beyond perpendicular fields. In an embodiment, asymmetric positioning of three transducer arrays is contemplated wherein one pair of the three transducer arrays may deliver alternating electrical fields and then another pair of the three transducer arrays may deliver the alternating electrical fields, and the remaining pair of the three transducer arrays may deliver the alternating electrical fields.

In-vivo and in-vitro studies show that the efficacy of TTFields therapy increases as the intensity of the electrical field increases. Therefore, optimizing array placement on the patient's scalp to increase the intensity in the diseased region of the brain is standard practice for the Optune system. Array placement optimization may be performed by "rule of thumb" (e.g., placing the arrays on the scalp as close to the tumor as possible), measurements describing the geometry of the patient's head, tumor dimensions, and/or tumor location. Measurements used as input may be derived from image data. Image data is intended to include any type of visual data, such as for example, single-photon emission computed tomography (SPECT) image data, x-ray computed tomography (x-ray CT) data, magnetic resonance imaging (MRI) data, positron emission tomography (PET) data, data that may be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). Optimization may rely on an understanding of how the electrical field distributes within, for example, the head as a function of the positions of the array and, in some aspects, take account for variations in the electrical property distributions within the heads of different patients. Transducer array placement positions may be optimized to treat any portion of the body (e.g., head, torso, etc.) of a patient/subject.

Optimized transducer array placement positions may be determined and recommended to a patient/subject, for example, when the patient/subject is attempting to place one or more transducer arrays at/on any portion of the body (e.g., head, torso, etc.) of the patient/subject. For example, a transducer array placement guidance/assistance tool may be used to compare, in real-time, image data (e.g., one or more images, video, a representation/avatar, etc.) of a portion of the body (e.g., head, torso, etc.) of a patient/subject that depicts the placement of one or more transducer arrays on the surface (skin) of the patient/subject, to a transducer array layout map that includes optimized and/or recommended areas for placement of one or more transducer arrays on the surface (skin) of the patient/subject. The transducer array placement guidance/assistance tool may be used to guide/instruct the patient/subject on where/how to place and/or move transducer arrays for optimal TTFields treatment.

FIG. 1 shows an example apparatus 100 for electrotherapeutic treatment. Generally, the apparatus 100 may be a portable battery or power supply operated device which produces alternating electrical fields within the body by means of non-invasive surface transducer arrays. The apparatus 100 may comprise an electrical field generator 102 and one or more transducer arrays 104. The apparatus 100 may be configured to generate tumor treatment fields (TTFields) (e.g., at 150 kHz) via the electrical field generator 102 and deliver the TTFields to an area of the body through the one or more transducer arrays 104. The electrical field generator 102 may be a battery and/or power supply operated device. In an embodiment, the one or more transducer arrays 104 are uniformly shaped. In an embodiment, the one or more transducer arrays 104 are not uniformly shaped.

The electrical field generator 102 may comprise a processor 106 in communication with a signal generator 108. The electrical field generator 102 may comprise control software 110 configured for controlling the performance of the processor 106 and the signal generator 108.

The signal generator 108 may generate one or more electric signals in the shape of waveforms or trains of pulses. The signal generator 108 may be configured to generate an alternating voltage waveform at frequencies in the range from about 50 KHz to about 500 KHz (preferably from about 100 KHz to about 300 KHz) (e.g., the TTFields). The voltages are such that the electrical field intensity in tissue to be treated is in the range of about 0.1 V/cm to about 10 V/cm.

One or more outputs 114 of the electrical field generator 102 may be coupled to one or more conductive leads 112 that are attached at one end thereof to the signal generator 108. The opposite ends of the conductive leads 112 are connected to the one or more transducer arrays 104 that are activated by the electric signals (e.g., waveforms). The conductive leads 112 may comprise standard isolated conductors with a flexible metal shield and may be grounded to prevent the spread of the electrical field generated by the conductive leads 112. The one or more outputs 114 may be operated sequentially. Output parameters of the signal generator 108 may comprise, for example, an intensity of the field, a frequency of the waves (e.g., treatment frequency), and a maximum allowable temperature of the one or more transducer arrays 104. The output parameters may be set and/or determined by the control software 110 in conjunction with the processor 106. After determining a desired (e.g., optimal) treatment frequency, the control software 110 may cause the processor 106 to send a control signal the signal generator 108 that causes the signal generator 108 to output the desired treatment frequency to the one or more transducer arrays 104.

The one or more transducer arrays 104 may be configured in a variety of shapes and positions so as to generate an electrical field of the desired configuration, direction and intensity at a target volume so as to focus treatment. The one or more transducer arrays 104 may be configured to deliver two perpendicular field directions through a volume of interest.

The one or more transducer arrays 104 arrays may comprise one or more electrodes 116. The one or more electrodes 116 may be made from any material with a high dielectric constant. The one or more electrodes 116 may comprise, for example, one or more insulated ceramic discs. The electrodes 116 may be biocompatible and coupled to a flexible circuit board 118. The electrodes 116 may be configured so as to not come into direct contact with the skin as the electrodes 116 are separated from the skin by a layer of conductive hydrogel (not shown) (similar to that found on electrocardiogram pads).

In alternative embodiments, the transducer arrays 104 may include only one single electrode element 106. In one example, the single electrode element is a flexible organic material or flexible organic composite positioned on a substrate. In another example, the transducer array 104 may include a flexible organic material or flexible organic composite without a substrate.

The electrodes 116, the hydrogel, and the flexible circuit board 118 may be attached to a hypo-allergenic medical adhesive bandage 120 to keep the one or more transducer arrays 104 in place on the body and in continuous direct contact with the skin. Each transducer array 104 may comprise one or more thermistors (not shown), for example 8 thermistors, (accuracy±1° C.) to measure skin temperature beneath the transducer arrays 104. The thermistors may be configured to measure skin temperature periodically, for example, every second. The thermistors may be read by the control software 110 while the TTFields are not being delivered in order to avoid any interference with the temperature measurements.

If the temperature measured is below a pre-set maximum temperature (Tmax), for example 38.5-40.0° C.±0.3° C., between two subsequent measures, the control software 110 may increase current until the current reaches maximal treatment current (for example, 4 Amps peak-to-peak). If the temperature reaches Tmax+0.3° C. and continues to rise, the control software 110 may lower the current. If the temperature rises to 41° C., the control software 110 may shut off the TTFields therapy and an overheating alarm may be triggered.

Figure 2:
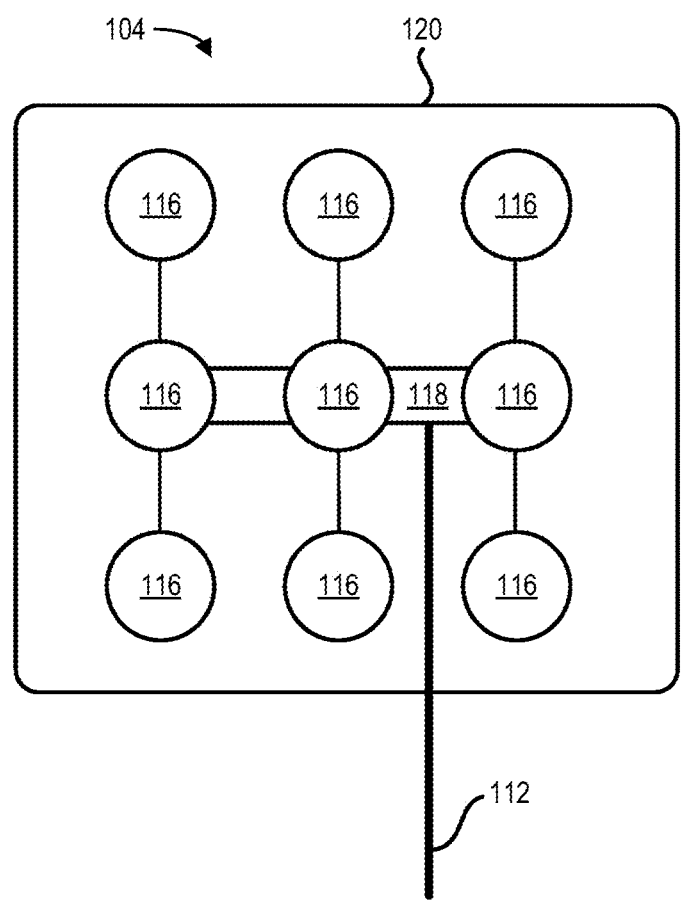
FIG. 2 shows an example transducer array.

The one or more transducer arrays 104 may vary in size and may comprise varying numbers of electrodes 116, based on patient body sizes and/or different therapeutic treatments. For example, in the context of the chest of a patient, small transducer arrays may comprise 13 electrodes each, and large transducer arrays may comprise 20 electrodes each, with the electrodes serially interconnected in each array. For example, as shown in FIG. 2, in the context of the head of a patient, each transducer array may comprise 9 electrodes each, with the electrodes serially interconnected in each array.

A status of the apparatus 100 and monitored parameters may be stored a memory (not shown) and may be transferred to a computing device over a wired or wireless connection. The apparatus 100 may comprise a display (not shown) for displaying visual indicators, such as, power on, treatment on, alarms, and low battery.

FIG. 3A and FIG. 3B illustrate an example application of the apparatus 100. A transducer array 104a and a transducer array 104b are shown, each incorporated into a hypo-allergenic medical adhesive bandage 120a and 120b, respectively. The hypo-allergenic medical adhesive bandages 120a and 120b are applied to skin surface 302. A tumor 304 is located below the skin surface 302 and bone tissue 306 and is located within brain tissue 308. The electrical field generator 102 causes the transducer array 104a and the transducer array 104b to generate alternating electrical fields 310 within the brain tissue 308 that disrupt rapid cell division exhibited by cancer cells of the tumor 304. The alternating electrical fields 310 have been shown in non-clinical experiments to arrest the proliferation of tumor cells and/or to destroy them. Use of the alternating electrical fields 310 takes advantage of the special characteristics, geometrical shape, and rate of dividing cancer cells, which make them susceptible to the effects of the alternating electrical fields 310. The alternating electrical fields 310 alter their polarity at an intermediate frequency (on the order of 100-300 kHz). The frequency used for a particular treatment may be specific to the cell type being treated (e.g., 150 kHz for MPM). The alternating electrical fields 310 have been shown to disrupt mitotic spindle microtubule assembly and to lead to dielectrophoretic dislocation of intracellular macromolecules and organelles during cytokinesis. These processes lead to physical disruption of the cell membrane and to programmed cell death (apoptosis).

Because the effect of the alternating electrical fields 310 is directional with cells dividing parallel to the field affected more than cells dividing in other directions, and because cells divide in all directions, alternating electrical fields 310 may be delivered through two pairs of transducer arrays 104 that generate perpendicular fields within the treated tumor. More specifically, one pair of transducer arrays 104 may be located to the left and right (LR) of the tumor, and the other pair of transducer arrays 104 may be located anterior and posterior (AP) to the tumor. Cycling the alternating electrical fields 310 between these two directions (e.g., LR and AP) ensures that a maximal range of cell orientations is targeted. In an embodiment, the alternating electrical fields 310 may be delivered according to a symmetric setup of transducer arrays 104 (e.g., four total transducer arrays 104, two matched pairs). In another embodiment, the alternating electrical fields 310 may be delivered according to an asymmetric setup of transducer arrays 104 (e.g., three total transducer arrays 104). An asymmetric setup of transducer arrays 104 may engage two of the three transducer arrays 104 to deliver the alternating electrical fields 310 and then switch to another two of the three transducer arrays 104 to deliver the alternating electrical fields 310, and the like.

In-vivo and in-vitro studies show that the efficacy of TTFields therapy increases as the intensity of the electrical field increases. The methods, systems, and apparatuses described are configured for optimizing array placement on the patient's scalp to increase the intensity in the diseased region of the brain.

Figure 4A:
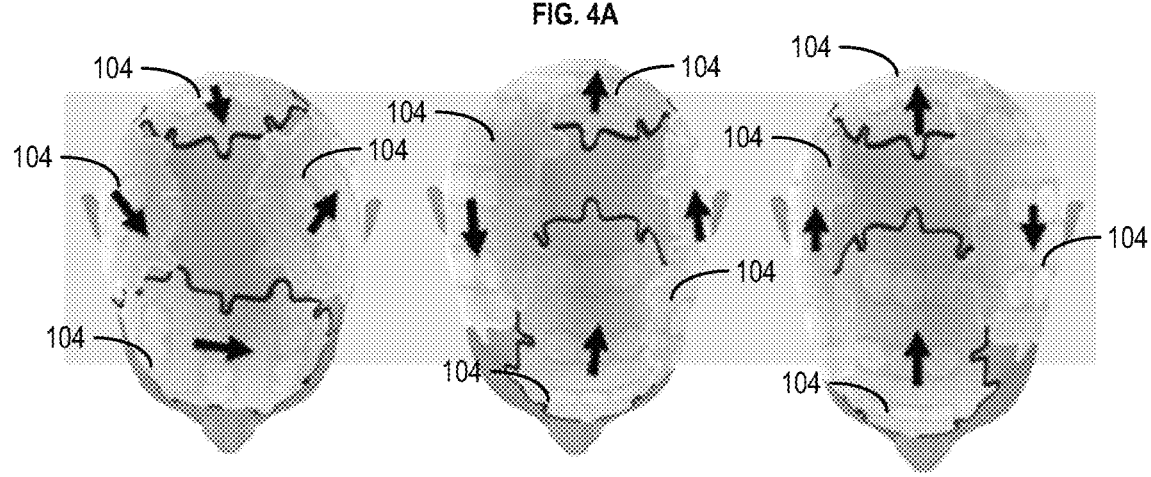
FIG. 4A shows transducer arrays placed on a patient's head.
Figure 4B:
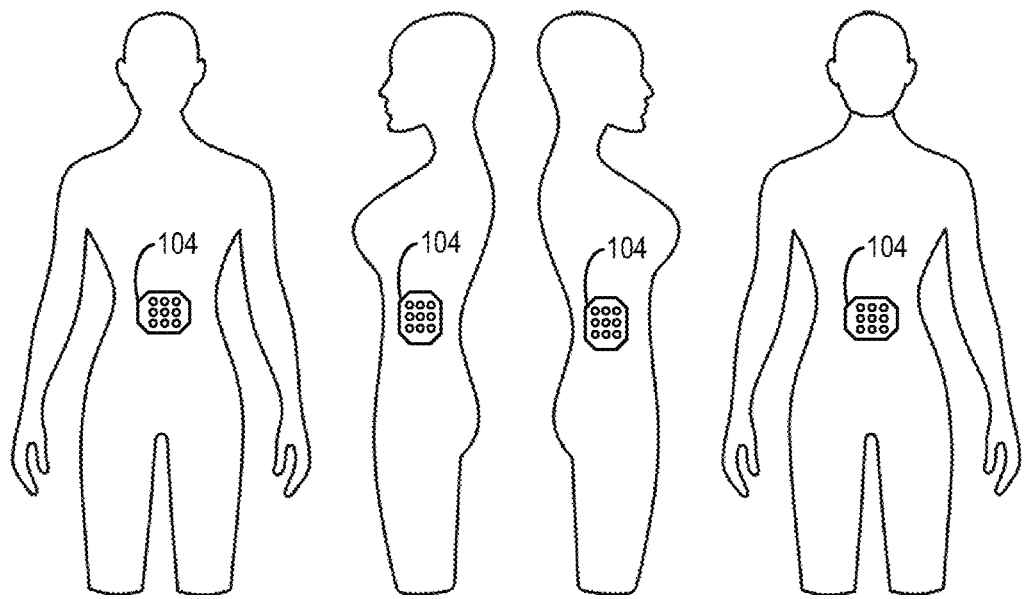
FIG. 4B shows transducer arrays placed on a patient's abdomen.
Figure 5A:
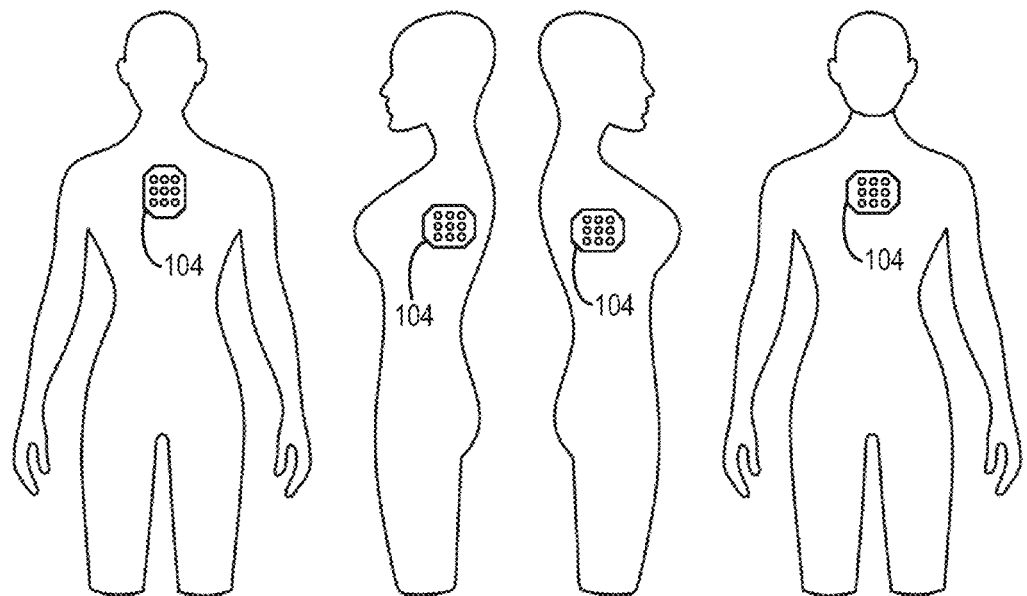
FIG. 5A, the transducer arrays placed on a patient's torso.
Figure 5B:
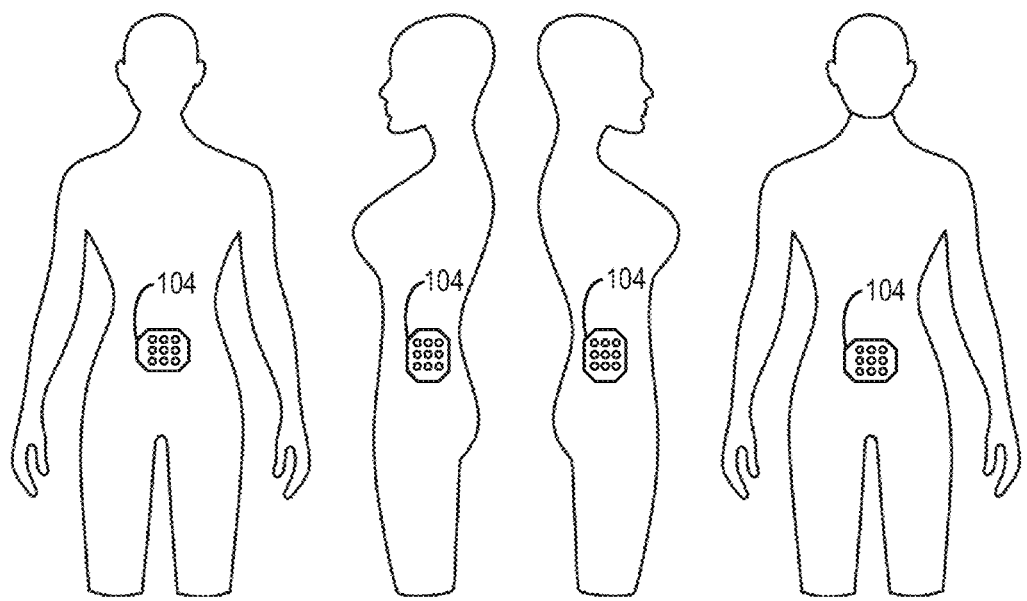
FIG. 5B shows transducer arrays placed on a patient's pelvis

As shown in FIG. 4A, the transducer arrays 104 may be placed on a patient's head. As shown in FIG. 4B, the transducer arrays 104 may be placed on a patient's abdomen. As shown in FIG. 5A, the transducer arrays 104 may be placed on a patient's torso. As shown in FIG. 5B, the transducer arrays 104 may be placed on a patient's pelvis. Placement of the transducer arrays 104 on other portions of a patient's body (e.g., arm, leg, etc.) is specifically contemplated.

Figure 6:
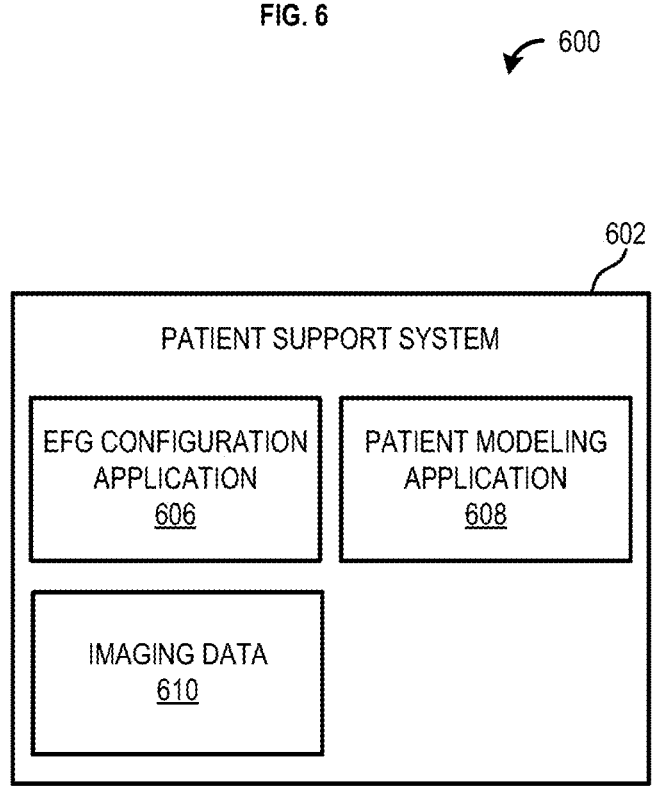
FIG. 6 is a block diagram depicting an electrical field generator and a patient support system.

FIG. 6 is a block diagram depicting non-limiting examples of a system 600 comprising a patient support system 602. The patient support system 602 may comprise one or multiple computers configured to operate and/or store an electrical field generator (EFG) configuration application 606, a patient modeling application 608, and/or imaging data 610. The patient support system 602 may comprise for example, a computing device. The patient support system 602 may comprise for example, a laptop computer, a desktop computer, a mobile phone (e.g., smartphone), a tablet, and the like.

The patient modeling application 608 may be configured to generate a three-dimensional model of a portion of a body of a patient (e.g., a patient model) according to the imaging data 610. The imaging data 610 may comprise any type of visual data, such as for example, single-photon emission computed tomography (SPECT) image data, x-ray computed tomography (x-ray CT) data, magnetic resonance imaging (MRI) data, positron emission tomography (PET) data, data that may be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). The patient modeling application 608 may also be configured to generate a three-dimensional array layout map based on the patient model and one or more electrical field simulations.

Figure 7:
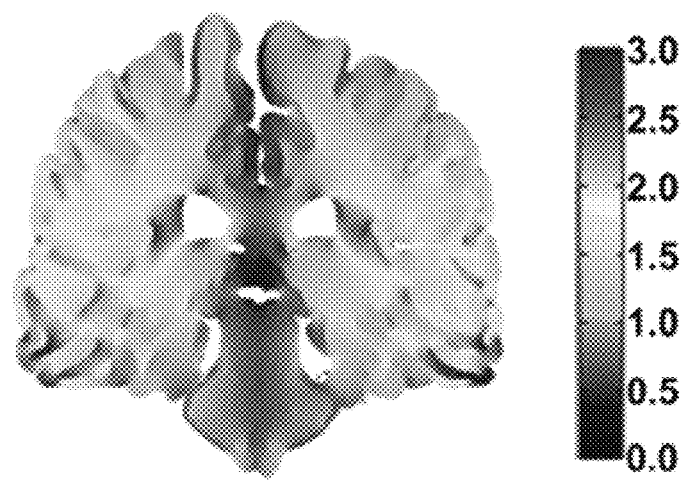
FIG. 7 illustrates electrical field magnitude and distribution (in V/cm) shown in coronal view from a finite element method simulation model.

In order to properly optimize array placement on a portion of a patient's body, the imaging data 610, such as MRI imaging data, may be analyzed by the patient modeling application 608 to identify a region of interest that comprises a tumor. In the context of a patient's head, to characterize how electrical fields behave and distribute within the human head, modeling frameworks based on anatomical head models using Finite Element Method (FEM) simulations may be used. These simulations yield realistic head models based on magnetic resonance imaging (MRI) measurements and compartmentalize tissue types such as skull, white matter, gray matter, and cerebrospinal fluid (CSF) within the head. Each tissue type may be assigned dielectric properties for relative conductivity and permittivity, and simulations may be run whereby different transducer array configurations are applied to the surface of the model in order to understand how an externally applied electrical field, of preset frequency, will distribute throughout any portion of a patient's body, for example, the brain. The results of these simulations, employing paired array configurations, a constant current, and a preset frequency of 200 kHz, have demonstrated that electrical field distributions are relatively non-uniform throughout the brain and that electrical field intensities exceeding 1 V/cm are generated in most tissue compartments except CSF. These results are obtained assuming total currents with a peak-to-peak value of 1800 milliamperes (mA) at the transducer array-scalp interface. This threshold of electrical field intensity is sufficient to arrest cellular proliferation in glioblastoma cell lines. Additionally, by manipulating the configuration of paired transducer arrays, it is possible to achieve an almost tripling of electrical field intensity to a particular region of the brain as shown in FIG. 7. FIG. 7 illustrates electrical field magnitude and distribution (in V/cm) shown in coronal view from a finite element method simulation model. This simulation employs a left-right paired transducer array configuration.

Figures 8A, 8B:
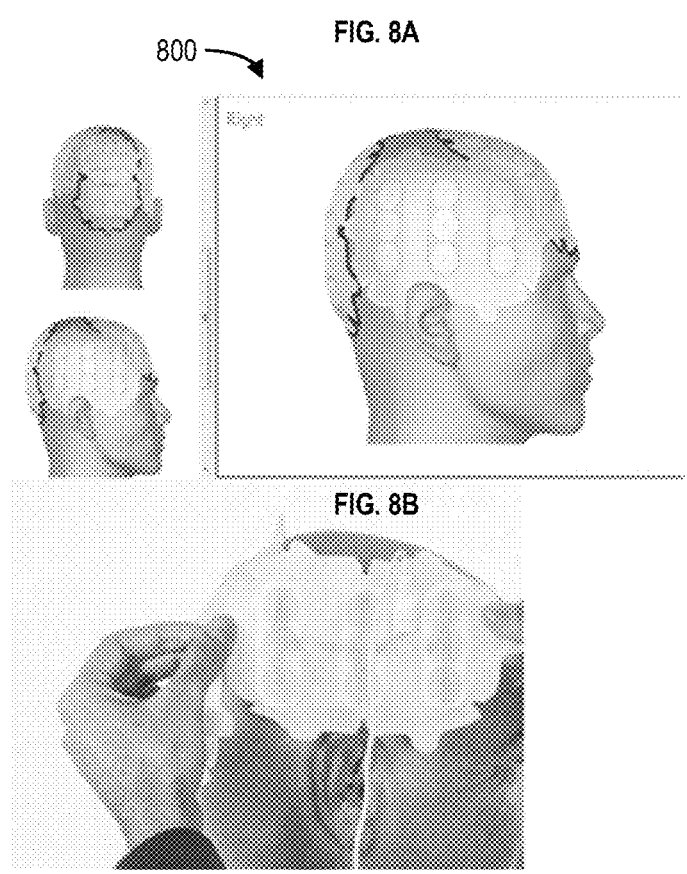
FIG. 8A shows a three-dimensional array layout map 800.
FIG. 8B shows placement of transducer arrays on the scalp of a patient.

In an aspect, the patient modeling application 608 may be configured to determine a desired (e.g., optimal) transducer array layout for a patient based on the location and extent of the tumor. For example, initial morphometric head size measurements may be determined from the T1 sequences of a brain MRI, using axial and coronal views. Postcontrast axial and coronal MRI slices may be selected to demonstrate the maximal diameter of enhancing lesions. Employing measures of head size and distances from predetermined fiducial markers to tumor margins, varying permutations and combinations of paired array layouts may be assessed in order to generate the configuration which delivers maximal electrical field intensity to the tumor site. As shown in FIG. 8A, the output may be a three-dimensional array layout map 800. The three-dimensional array layout map 800 may be used by the patient and/or caregiver in arranging arrays on the scalp during the normal course of TTFields therapy as shown in FIG. 8B.

In an aspect, the patient modeling application 608 may be configured to determine the three-dimensional array layout map for a patient. MRI measurements of the portion of the patient that is to receive the transducer arrays may be determined. By way of example, the MRI measurements may be received via a standard Digital Imaging and Communications in Medicine (DICOM) viewer. MRI measurement determination may be performed automatically, for example by way of artificial intelligence techniques or may be performed manually, for example by way of a physician.

Figure 9A:
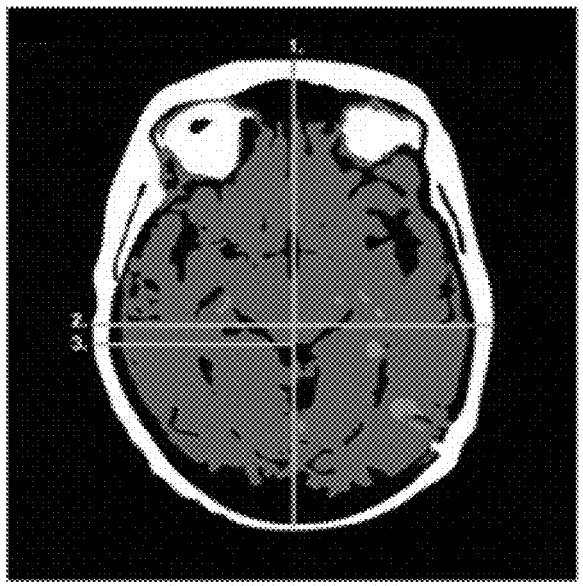
FIG. 9A shows an axial T1 sequence slice containing most apical image, including orbits used to measure head size.
Figure 9B:
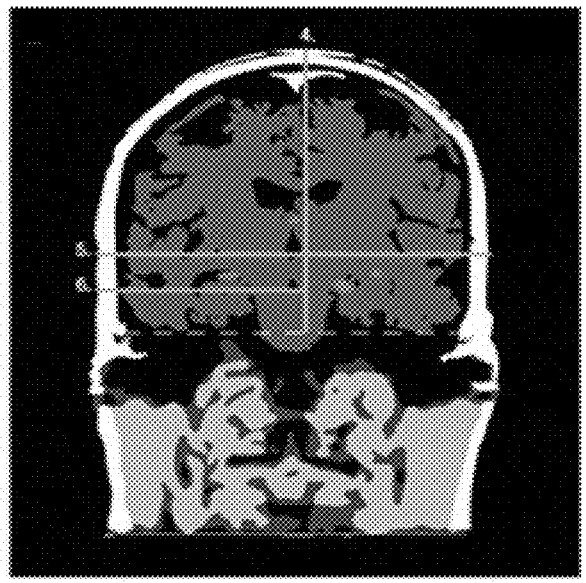
FIG. 9B shows a coronal T1 sequence slice selecting image at level of ear canal used to measure head size.
Figure 9C:
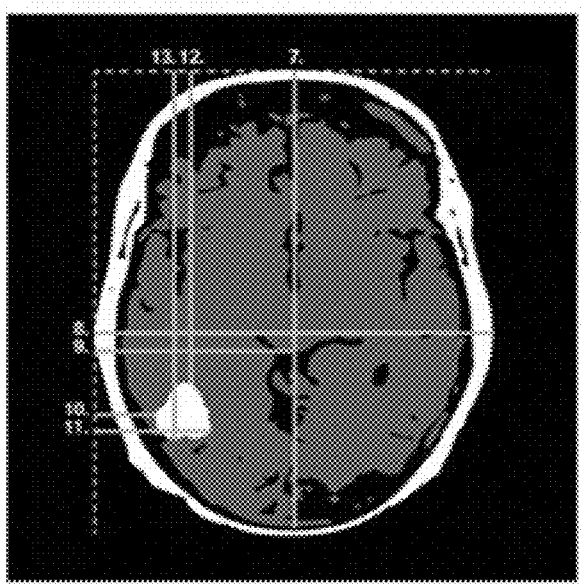
FIG. 9C shows a postcontrast T1 axial image shows maximal enhancing tumor diameter used to measure tumor location.
Figure 9D:
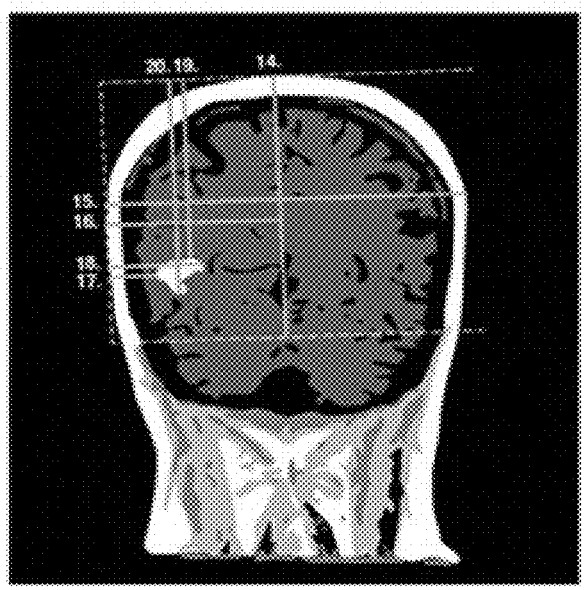
FIG. 9D shows a postcontrast T1 coronal image shows maximal enhancing tumor diameter used to measure tumor location.

Manual MRI measurement determination may comprise receiving and/or providing MRI data via a DICOM viewer. The MRI data may comprise scans of the portion of the patient that contains a tumor. By way of example, in the context of the head of a patient, the MRI data may comprise scans of the head that comprise one or more of a right fronto-temporal tumor, a right parieto-temporal tumor, a left fronto-temporal tumor, a left parieto-occipital tumor, and/or a multi-focal midline tumor. FIG. 9A, FIG. 9B, FIG. 9C, and FIG. 9D show example MRI data showing scans of the head of a patient. FIG. 9A shows an axial T1 sequence slice containing most apical image, including orbits used to measure head size. FIG. 9B shows a coronal T1 sequence slice selecting image at level of ear canal used to measure head size. FIG. 9C shows a postcontrast T1 axial image shows maximal enhancing tumor diameter used to measure tumor location. FIG. 9D shows a postcontrast T1 coronal image shows maximal enhancing tumor diameter used to measure tumor location. MRI measurements may commence from fiducial markers at the outer margin of the scalp and extend tangentially from a right-, anterior-, superior origin. Morphometric head size may be estimated from the axial T1 MRI sequence selecting the most apical image which still included the orbits (or the image directly above the superior edge of the orbits)

In an aspect, the MRI measurements may comprise, for example, one or more of, head size measurements and/or tumor measurements. In an aspect, one or more MRI measurements may be rounded to the nearest millimeter and may be provided to a transducer array placement module (e.g., software) for analysis. The MRI measurements may then be used to generate the three-dimensional array layout map (e.g., three-dimensional array layout map 800).

The MRI measurements may comprise one or more head size measurements such as: a maximal antero-posterior (A-P) head size, commencing measurement from the outer margin of the scalp; a maximal width of the head perpendicular to the A-P measurement: right to left lateral distance; and/or a distance from the far most right margin of the scalp to the anatomical midline.

The MRI measurements may comprise one or more head size measurements such as coronal view head size measurements. Coronal view head size measurements may be obtained on the T1 MRI sequence selecting the image at the level of the ear canal (FIG. 9B). The coronal view head size measurements may comprise one or more of: a vertical measurement from the apex of the scalp to an orthogonal line delineating the inferior margin of the temporal lobes; a maximal right to left lateral head width; and/or a distance from the far right margin of the scalp to the anatomical midline.

The MRI measurements may comprise one or more tumor measurements, such as tumor location measurements. The tumor location measurements may be made using T1 postcontrast MRI sequences, firstly on the axial image demonstrating maximal enhancing tumor diameter (FIG. 9C). The tumor location measurements may comprise one or more of: a maximal A-P head size, excluding the nose; a maximal right to left lateral diameter, measured perpendicular to the A-P distance; a distance from the right margin of the scalp to the anatomical midline; a distance from the right margin of the scalp to the closest tumor margin, measured parallel to the right-left lateral distance and perpendicular to the A-P measurement; a distance from the right margin of the scalp to the farthest tumor margin, measured parallel to the right-left lateral distance, perpendicular to the A-P measurement; a distance from the front of the head, measured parallel to the A-P measurement, to the closest tumor margin; and/or a distance from the front of the head, measured parallel to the A-P measurement, to the farthest tumor margin.

The one or more tumor measurements may comprise coronal view tumor measurements. The coronal view tumor measurements may comprise identifying the postcontrast T1 MRI slice featuring the maximal diameter of tumor enhancement (FIG. 9D). The coronal view tumor measurements may comprise one or more of: a maximal distance from the apex of the scalp to the inferior margin of the cerebrum. In anterior slices, this would be demarcated by a horizontal line drawn at the inferior margin of the frontal or temporal lobes, and posteriorly, it would extend to the lowest level of visible tentorium; a maximal right to left lateral head width; a distance from the right margin of the scalp to the anatomical midline; a distance from the right margin of the scalp to the closest tumor margin, measured parallel to the right-left lateral distance; a distance from the right margin of the scalp to the farthest tumor margin, measured parallel to the right-left lateral distance; a distance from the apex of the head to the closest tumor margin, measured parallel to the superior apex to inferior cerebrum line; and/or a distance from the apex of the head to the farthest tumor margin, measured parallel to the superior apex to inferior cerebrum line.

Other MRI measurements may be used, particularly when the tumor is present in another portion of the patient's body.

The MRI measurements may be used by the patient modeling application 608 to generate a patient model. The patient model may then be used to determine the three-dimensional array layout map (e.g., three-dimensional array layout map 800). Continuing the example of a tumor within the head of a patient, a healthy head model may be generated which serves as a deformable template from which patient models may be created. When creating a patient model, the tumor may be segmented from the patient's MRI data (e.g., the one or more MRI measurements). Segmenting the MRI data identifies the tissue type in each voxel, and electric properties may be assigned to each tissue type based on empirical data. Table 1 shows standard electrical properties of tissues that may be used in simulations. The region of the tumor in the patient MRI data may be masked, and non-rigid registration algorithms may be used to register the remaining regions of the patient head on to a 3D discrete image representing the deformable template of the healthy head model. This process yields a non-rigid transformation that maps the healthy portion of the patient's head into the template space, as well as the inverse transformation that maps the template into the patient space. The inverse transformation is applied to the 3D deformable template to yield an approximation of the patient head in the absence of a tumor. Finally, the tumor (referred to as a region-of-interest (ROI)) is planted back into the deformed template to yield the full patient model. The patient model may be a digital representation in three-dimensional space of the portion of the patient's body, including internal structures, such as tissues, organs, tumors, etc.

TABLE 1

| Tissue Type | Conductivity, S/m | Relative Permittivity |
| --- | --- | --- |
| Scalp | 0.3 | 5000 |
| Skull | 0.08 | 200 |
| Cerebrospinal fluid | 1.79 | 110 |
| Gray matter | 0.25 | 3000 |
| White matter | 0.12 | 2000 |
| Enhancing tumor | 0.24 | 2000 |
| Enhancing nontumor | 0.36 | 1170 |
| Resection cavity | 1.79 | 110 |
| Necrotic tumor | 1 | 110 |
| Hematoma | 0.3 | 2000 |
| Ischemia | 0.18 | 2500 |
| Atrophy | 1 | 110 |
| Air | 0 | 0 |

Delivery of TTFields may then be simulated by the patient modeling application 608 using the patient model. Simulated electrical field distributions, dosimetry, and simulation-based analysis are described in U.S. Patent Application Publication No. 20190117956 A1 and Ballo et al., "Correlation of Tumor treating Fields Dosimetry to Survival Outcomes in Newly Diagnosed Glioblastoma: A Large-Scale Numerical Simulation-Based Analysis of Data from the Phase 3 EF-14 Randomized Trial," International Journal of Radiation Oncology, Biology, Physics, 2019; 104(5), pp. 1106-1113.

To ensure systematic positioning of the transducer arrays relative to the tumor location, a reference coordinate system may be defined. For example, a transversal plane may initially be defined by conventional LR and anteroposterior (AP) positioning of the transducer arrays. The left-right direction may be defined as the x-axis, the AP direction may be defined as the y-axis, and the cranio-caudal direction normal to the xy-plane may be defined as the z-axis.

After defining the coordinate system, transducer arrays may be virtually placed on the patient model with their centers and longitudinal axes in the xy-plane. A pair of transducer arrays may be systematically rotated around the z-axis of the head model, i.e. in the xy-plane, from 0 to 180 degrees, thereby covering the entire circumference of the head (by symmetry). The rotation interval may be, for example, 15 degrees, corresponding to approximately 2 cm translations, giving a total of twelve different positions in the range of 180 degrees. Other rotation intervals are contemplated. Electrical field distribution calculations may be performed for each transducer array position relative to tumor coordinates.

Electrical field distribution in the patient model may be determined by the patient modeling application 608 using a finite element (FE) approximation of electrical potential. In general, the quantities defining a time-varying electromagnetic field are given by the complex Maxwell equations. However, in biological tissues and at the low to intermediate frequency of TTFields (f=200 kHz), the electromagnetic wavelength is much larger than the size of the head and the electric permittivity F is negligible compared to the real-valued electric conductivity $\sigma$, i.e., where $\omega=2\pi f$ is the angular frequency. This implies that the electromagnetic propagation effects and capacitive effects in the tissue are negligible, so the scalar electric potential may be well approximated by the static Laplace equation $\nabla \cdot (\sigma \nabla \phi)=0$, with appropriate boundary conditions at the electrodes and skin. Thus, the complex impedance is treated as resistive (i.e. reactance is negligible) and currents flowing within the volume conductor are, therefore, mainly free (Ohmic) currents. The FE approximation of Laplace's equation may be calculated using software, such as SimNIBS software (simnibs.org). Computations based on the Galerkin method and the residuals for the conjugate gradient solver are required to be <1E-9. Dirichlet boundary conditions were used with the electric potential was set to (arbitrarily chosen) fixed values at each set of electrode arrays. The electric (vector) field may be calculated as the numerical gradient of the electric potential and the current density (vector field) may be computed from the electrical field using Ohm's law. The potential difference of the electrical field values and the current densities may be linearly rescaled to ensure a total peak-to-peak amplitude for each array pair of 1.8 A, calculated as the (numerical) surface integral of the normal current density components over all triangular surface elements on the active electrode discs. The "dose" of TTFields may calculated as the intensity (L2 norm) of the field vectors. The modeled current may be assumed to be provided by two separate and sequentially active sources each connected to a pair of 3×3 transducer arrays. The left and posterior arrays may be defined to be sources in the simulations, while the right and anterior arrays were the corresponding sinks, respectively. However, as TTFields employ alternating fields, this choice is arbitrary and does not influence the results.

An average electrical field strength generated by transducer arrays placed at multiple locations on the patient may be determined by the patient modeling application 608 for one or more tissue types. In an aspect, the transducer array position that corresponds to the highest average electrical field strength in the tumor tissue type(s) may be selected as a desired (e.g., optimal) transducer array position for the patient. For example, a method for determining an optimal transducer array layout may include determining a region-of-interest (ROI) within a 3D model of a portion of a subject's body. Based on a center of the ROI, a plane that transverses the portion of the subject's body may be determined, wherein the plane comprises a plurality of pairs of positions along a contour of the plane. The method may include adjusting, based on an anatomical restriction, one or more positions of the plurality of pairs of positions to generate a modified plane. The anatomical restriction may be based on an anatomical feature of the portion of the subject's body. For example, a first electrical field generated by a first transducer array may be simulated at a first position, a second electrical field generated by a second transducer array may be simulated at a second position opposite the first position, and, based on the first electrical field and the second electrical field, the simulated electrical field distribution may be determined. In some instances, a third electrical field generated by the first transducer array may be simulated at a third position, and a fourth electrical field generated by the second transducer array may be simulated at a fourth position opposite the third position, and, based on the third electrical field and the fourth electrical field, the simulated electrical field distribution may be determined. The method may include determining, for each pair of positions of the plurality of pairs positions on the modified plane, a simulated electrical field distribution, and determining, based on the simulated electrical field distributions, a dose metric for each pair of positions of the plurality of pairs positions. One or more sets of pairs of positions of the plurality of pairs of positions that satisfy an angular restriction between pairs of transducer arrays may be determined. For example, the angular restriction may be and/or indicate an orthogonal angle between the plurality of pairs of transducer arrays. The angular restriction, for example, may be and/or indicate a range of an angle between the plurality of pairs of transducer arrays. Based on the dose metrics and the one or more sets of pairs of positions that satisfy the angular restriction, one or more candidate transducer array layout maps. A simulated orientation or a simulated position for at least one transducer array at least one position of the one or more candidate transducer array layout maps me be adjusted. Based on adjusting the simulated orientation or the simulated position for the at least one transducer array, a final transducer array layout map may be determined.

The patient model may be modified, for example, based on the final transducer array layout map, to include an indication of the desired transducer array position. The resulting patient model, comprising the indication(s) of the desired transducer array position(s), may be referred to as the three-dimensional array layout map (e.g., three-dimensional array layout map 800). The three-dimensional array layout map may thus comprise a digital representation, in three-dimensional space, of the portion of the patient's body, an indication of tumor location, an indication of a position for placement of one or more transducer arrays, combinations thereof, and the like.

In one embodiment, a three-dimensional transducer array layout map with one or more recommended transducer placement positions may be generated and provided to the patient in a digital form and/or a physical form. The patient, and/or a patient caregiver, may use the three-dimensional transducer array layout map to affix one or more transducer arrays to an associated portion of the patient's body (e.g., head, torso, etc.).

In another embodiment, an augmented reality assistance tool may use the three-dimensional array layout map to assist the patient and/or a patient caregiver to affix one or more transducer arrays to an associated portion of the patient's body (e.g., head, torso, etc.). For example, transducer array placement positions, such as optimized transducer array placement positions, may be determined and representations of transducer array patches, disk, and/or the like may be presented on the surface of a patient/subject virtual model based on the determined positions. For example, the augmented reality assistance tool may be used to instruct a user (e.g., a patient, a patient caregiver, etc.) to capture images (e.g., images, video, etc.) of a portion of the body (e.g., head, torso, etc.) of a patient/subject for transducer array placement. The images (e.g., images, video, etc.) may be registered, for example in real-time, to a virtual patient model. Once registered, the representations of transducer array patches, disk, additional landmarks, and/or the like may be virtually displayed (e.g., overlaid using augmented reality, etc.) relative to the images and/or patient model to enable transducer arrays to be placed (at the optimized positions) on the surface (skin) of the patient with high accuracy.

In some instances, a transducer array placement guidance/assistance tool may guide/assist a patient/subject with positioning transducer arrays on the patient/subject. For example, when the patient/subject is placing one or more transducer arrays at/on any portion of their body (e.g., head, torso, etc.), if the one or more transducer arrays are not properly placed in/at positions that optimize TTFields therapy/treatment, a three-dimensional array layout map may be used to recommend correct movements and/or placement positions for the one or more transducer arrays.

In some instances, virtual reality assistance tools may be used to generate a 3D model with the optimized transducer array placement positions and/or to guide/assist a patient/subject to place one or more arrays at the optimized transducer array placement positions. In one example, the virtual reality assistance tools maybe virtual reality headsets, virtual reality goggles, etc. For example, the three-dimensional transducer array layout map may be provided to the patient through the virtual reality assistance tools. Furthermore, the virtual reality assistance tools may be used to give feedback to the patient or caregiver regarding whether or not the one or more transducer arrays are properly placed in/at the optimized positions.

The methods described enable points within two-dimensional (2D) image data indicative of placement locations of the actual transducer arrays with respect to a patient/subject's body to be transformed to points in three-dimensional (3D) space. The two-dimensional (2D) image data may include images captured by a user device (e.g., a smartphone, a mobile device, a computing device, etc.) that depict the placement locations of the actual transducer arrays with respect to a patient/subject's body. The 3D points/coordinates indicative of the placement locations of the actual transducer arrays with respect to the patient/subject's body may be transformed and/or registered to 3D medical imaging coordinates, such as MRI coordinates, based on medical imaging data associated with the patient/subject. The placement locations of the actual transducer arrays may then be compared with one or more recommended transducer array placement locations previously determined from the medical imaging data to determine if the placement locations of the actual transducer arrays correspond to the one or more recommended transducer array placement locations.

For example, a patient/subject may use a user device (e.g., a smartphone, a mobile device, a computing device, etc.) to capture a plurality of images, from different vantage points and/or viewpoints, of a portion of a patient/subjects subject's body where one or more transducer arrays have been placed for TTFields therapy/treatment. The plurality of images may capture the placement position(s) of the one or more transducer arrays. Object recognition and/or the like may be used to analyze the plurality of images and determine the placement position(s) for the one or more transducer arrays. For example, object recognition and/or the like may be used determine/detect one or more landmarks (e.g., anatomical landmarks, artificial landmarks, etc.) from the plurality of images. The one or more landmarks may be used to determine the placement position(s) for the one or more transducer arrays.

In some instances, the portion of the patient/subjects subject's body may have one or more regions, such as the back of the patient's head, that are devoid of landmarks that may be determined/detected by object recognition and used to determine the placement position(s) for the one or more transducer arrays. Machine learning may be used to predict and/or estimate the placement position(s) for the one or more transducer arrays, for example, in scenarios where one or more portions of the one or more transducer arrays are not present and/or represented within the plurality of images. For example, a machine learning model may be trained to estimate the complete shape, configuration, and or placement of a transducer array when only one or more portions of the transducer array is present and/or represented within the plurality of images. Estimated shapes, configurations, and/or placement position(s)s of the one or more transducer arrays may be combined with the placement position(s) for the one or more transducer arrays determined from object recognition to determine the complete shape, configuration, and or placement of the one or more transducer arrays. The machine learning model may assign estimated points/coordinates to the estimated shapes, configurations, and/or placement position(s)s of the one or more transducer arrays.

Then, a three-dimensional (3D) points (e.g., coordinates) that represent and/or associated with the placement position(s) (and/or shape, configuration, etc.) for the one or more transducer arrays may be determined/generated. The 3D points (e.g., coordinates) may be transformed to 3D coordinates and/or used to determine 3D coordinates within an anatomical coordinate system (e.g., patient coordinate system, etc.), such as a 3D coordinates used for medical imaging (e.g., magnetic resonance imaging (MRI), x-ray computed tomography (x-ray CT) imaging, single-photon emission computed tomography (SPECT) imaging, positron emission tomography (PET) imaging, etc.) that incorporates anatomical planes (e.g., a sagittal plane, a coronal plane, a transverse plane, etc.). For example, the 3D points (e.g., coordinates) may be transformed to 3D coordinates associated with one or more medical images that are associated with the patient/subject.

The locations/positions where the one or more transducer arrays are placed, as determined and/or indicated by the 3D coordinates associated with the anatomical coordinate system, may be compared to optimized transducer array placement positions indicated by a 3D transducer array layout map. The optimized transducer array placement positions may be based on one or more TTFields treatment/therapy simulations performed based on the one or more medical images associated with the patient/subject. The optimized transducer array placement positions may be recommended to the patient/subject, for example, to promote optimal efficacy of TTFields therapy/treatment. For example, the locations/positions where the one or more transducer arrays are placed may be displayed (e.g., superimposed, overlaid, etc.) with the optimized (e.g., recommended, etc.) transducer array placement positions. In some instances, the locations/positions where the one or more transducer arrays are placed may be displayed (e.g., superimposed, overlaid, etc.) with representations of transducer array patches, disks, and/or the like at the optimized (e.g., recommended, etc.) transducer array placement positions.

In another embodiment, the locations/positions where the one or more transducer arrays are placed may be compared and displayed (e.g., superimposed, overlaid, etc.) with the one or more recommended transducer placement positions. In one example, the one or more transducer placements and the one or more recommended transducer placement positions may be displayed in an actual image and/or realistic depiction of the patient/subject and/or the portion of the patient's/subject's body. In another example, the one or more transducer placements and the one or more recommended transducer placement positions may be displayed in a representative image (e.g., avatar, etc.) of the patient/subject and/or the portion of the patient's/subject's body.

In one embodiment, the locations/positions where the one or more transducer arrays are placed may not match the one or more recommended transducer placement positions. For example, based on the comparing the 3D coordinates associated with the anatomical coordinate to the optimized transducer array placement positions indicated by the 3D transducer array layout map, a variance of at least one of the one or more placement positions for one or more transducer arrays from at least one of the one or more recommended transducer placement positions may be determined. To resolve the variance, any movement (e.g., corrective movement etc.) of the locations/positions where the one or more transducer arrays are placed that cause the locations/positions where the one or more transducer arrays are placed to match the one or more recommended transducer placement positions, may be sent to the patient/subject, for example, as a notification. The notification may be a visual notification, an audio notification, a textual notification, and/or the like.

Figure 10:
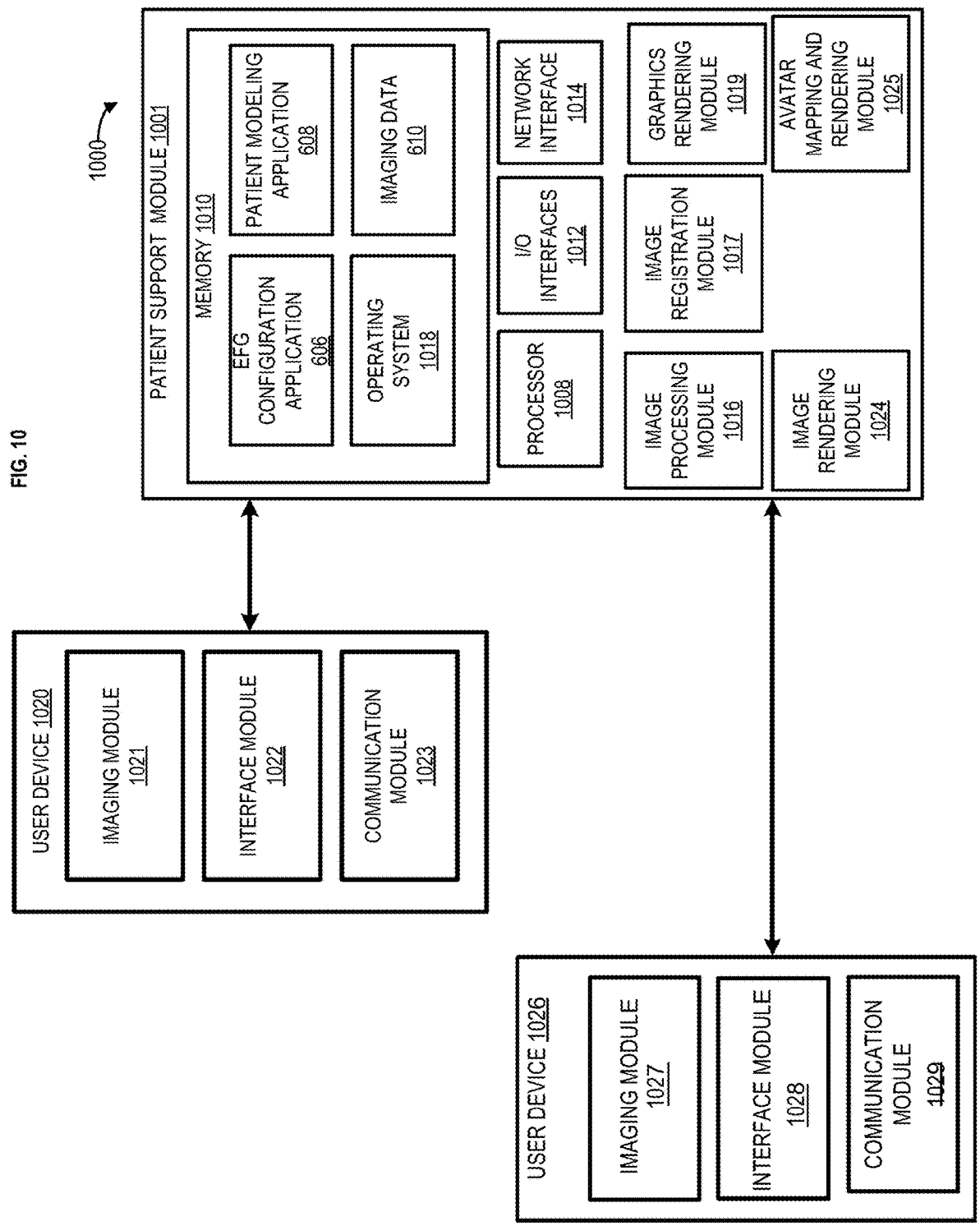
FIG. 10 shows an example system for guided transducer placements for TTFields.

FIG. 10 is an example system for guided transducer placements for TTFields. In some instances, components of the system 1000 may be implemented as a single device and/or the like. In some instances, components of the system 1000 may be implemented as separate devices/components in collective communication. In an aspect, some or all steps of any described method may be performed on and/or via components of the system 1000.

The system 1000 may include a user device 1020. The user device 1020 may be an electronic device such as a smartphone, a mobile device, a computing device, and/or the like capable of communicating with a patient support module 1001. The user device 1020 may include an imaging module 1021. The imaging module 1021 may include one or more image capturing devices, such as one or more video cameras that determine/capture a first set of image data (e.g., video data, static/still images, dynamic/interactive images, etc.) corresponding to the real world to the system 1000. In one example, the user device 1020 may be used to determine one or more recommended transducer placement positions. In some instances, the system 1000 may include multiple user devices (e.g., the second user device 1026) with imaging modules that share and/or exchange data/information, such as imaging data. The imaging module 1021 may capture image data that provides a real-time and real-world representation of a user (e.g., a patient, a subject, etc.), such as a real-time and/or real-world representation of the user and/or a portion (e.g., head, torso, etc.) of the user's body. For example, imaging module 1021 may be used to capture/take video images of a portion(s) of a user's body where (related to where) TTfields therapy is to be administered via one or more transducer arrays.

The user device 1020 may include an interface module 1022. The interface module 1022 may provide an interface to the user to interact with the user device 1020 and/or the patient support module 1001. The interface module 1022 may include one or more input devices/interfaces such as a keyboard, a pointing device (e.g., a computer mouse, remote control), a microphone, a joystick, a scanner, haptic sensing and/or tactile input devices, and/or the like.

The interface module 1022 may include one or more interfaces for presenting and/or receiving information to/from the user, such as user feedback. The interface module 1022 may include any software, hardware, and/or interfaces used to provide communication between the user and one or more of the user devices 1020, the patient support module 1001, and/or any other component of the system 1000. The interface module 1022 may include one or more audio device (e.g., stereos, speakers, microphones, etc.) for capturing/obtaining audio information and conveying audio information, such as audio information captured/obtained from the user and/or conveyed to the user. The interface module 1022 may include a graphical user interface (GUI), a web browser (e.g., Internet Explorer®, Mozilla Firefox®, Google Chrome®, Safari®, or the like), an application/API. The interface module 1022 may request and/or query various files from a local source and/or a remote source, such as the patient support module 1001.

The interface module 1022 may transmit/send data to a local or remote device/component of the system 1000 such as the patient support module 1001. The user device 1020 may include a communication module 1023. The communication module 1023 may enable the user device 1020 to communicate with components of the system 1000, such as the patient support module 1001 and/or another user device, via wired and/or wireless communication techniques. For example, the communication module 1023 may utilize any suitable wired communication technique, such as Ethernet, coaxial cable, fiber optics, and/or the like. The communication module 1023 may utilize any suitable long-range communication technique, such as Wi-Fi (IEEE 802.11), BLUETOOTH®, cellular, satellite, infrared, and/or the like. The communication module 1023 may utilize any suitable short-range communication technique, such as BLUETOOTH®, near-field communication, infrared, and the like.

The interface module 1022 may include one or more displays (e.g., monitors, head-up displays, head mounted displays. liquid crystal displays, organic light-emitting diode displays, active-matrix organic light-emitting diode displays, stereo displays, virtual reality displays, etc.) for displaying/presenting information to a user (e.g., a patient, a subject, etc.), such as an augmented reality and/or virtual image, a mirrored image, a superimposed image, and/or the like. For example, the interface module 1022 may display a representation of the user and/or a portion (e.g., head, torso, etc.) of the user's body based on the first set of image data captured by the imaging module 1021. In some instances, the representation of the user and/or a portion (e.g., head, torso, etc.) of the user's body may be an actual (e.g., mirrored) representation of the user and/or a portion (e.g., head, torso, etc.) of the user's body. In some instances, the representation of the user and/or a portion of the user's body may represent the user and/or a portion of the user's body from a different viewpoint, angle/position, field of view, and/or the like. In some instances, the representation of the user and/or a portion of the user's body may include an actual (e.g., mirrored) representation of the user and/or a portion of the user's body, and the user and/or a portion of the user's body from a different viewpoint, angle/position, field of view, and/or the like at the same time, such as a split view representation of the user and/or a portion of the user's body. In some instances, the representation of the user and/or a portion of the user's body may include a generic/replicated representations of the user and/or a portion of the user's body such as a generic image, a replicated image, a wired/stick image, virtual image (e.g., an avatar, etc.), and/or the like. To generate and/or display a generic/replicated representation of the user and/or a portion of the user's body such as a generic image, a replicated image, a wired/stick image, virtual image (e.g., an avatar, etc.), and/or the like, the user device may send the first set of image data (e.g., video data, static/still images, dynamic/interactive images, etc.) associated with a portion of the user's body (e.g., head, torso, etc.), captured by the imaging module 1021, to the patient support module 1001. In some instances, one or more user devices may send the image data (e.g., compiled image data, image data taken from one or more viewpoints, etc.) associated with the portion of the user's body (e.g., head, torso, etc.) to the patient support module 1001.

The patient support module 1001 may use the image data (and/or compiled image data) from the user device 1020 to determine a patient model associated with the user and determine transducer array placement positions, such as optimized transducer array placement positions, on the patient model where transducer arrays (or associated equipment such as patches, disk, array attachment supports, and/or the like) may be represented as one or more images superimposed/overlaid with the image data.

The system 1000 may include a second user device 1026. The second user device 1026 may be a different user device from the user device 1020, or the same user device as the user device 1020. The second user device 1026 may be used to determine the actual placements of one or more transduces. The user device 1026 may be an electronic device such as a smartphone, a mobile device, a computing device, a virtual reality assistance tool, and/or the like capable of communicating with a patient support module 1001. The second user device 1026 may include an interface module 1028. The interface module 1028 may provide an interface to the user to interact with the second user device 1026 and/or the patient support module 1001. The interface module 1028 may structure and/or function similarly to the interface module 1022.

The interface module 1028 may transmit/send data to a local or remote device/component of the system 1000 such as the patient support module 1001. The second user device 1026 may include a communication module 1029. The communication module 1029 may enable the second user device 1026 to communicate with components of the system 1000, such as the patient support module 1001 and/or another user device, via wired and/or wireless communication techniques. The communication module 1029 may structure and/or function similarly to the communication module 1023.

The second user device 1026 may include an imaging module 1027. The imaging module 1027 may include one or more image capturing devices, such as one or more cameras that determine/capture a second set of image data (e.g., static/still images, dynamic/interactive images, video, etc.). The imaging module 1027 may capture the image data that provides a real-time and/or real-world representation of a user (e.g., a patient, a subject, etc.), such as a real-time and/or real-world representation of the user and/or a portion (e.g., head, torso, etc.) of the user's body. For example, imaging module 1027 may be used to capture/take images and/or video of a portion(s) of a user's body where (related to where) TTFields therapy is to be administered via one or more transducer arrays.

To generate and/or display a representation of the user and/or a portion of the user's body, the second user device 1026 may send the image data (e.g., video data, static/still images, dynamic/interactive images, etc.) associated with the portion of the user's body (e.g., head, torso, etc.), captured by the imaging module 1027, to the patient support module 1001. The second set of image data may include a plurality of images taken from multiple vantage points, viewpoints, and/or the like associated with the portion of the user's body.

The image data may include data indicative of and/or determined from one or more tracking points/landmarks, such as anatomical landmarks and/or visual/artificial landmarks. For example, anatomical landmarks may include body locations (e.g., head, bones/ligaments, joints, etc.), and/or facial expression points (e.g., eyes, nose, eyebrows, etc.). Visual/artificial landmarks may include one or more indicators (e.g., stickers, marks/temporary tattoos, objects, etc.) placed at one or more locations/positions on the user and/or a portion of the user's body.

The patient support module 1001 may include a processor 1008. The processor 1008 may be a hardware device for executing software, particularly that stored in memory 1010. The processor 1008 may be any custom made or commercially available processor, a central processing unit (CPU), an auxiliary processor among several processors associated with the patient support module 1001, a semiconductor-based microprocessor (in the form of a microchip or chip set), or generally any device for executing software instructions. When the patient support module 1001 is in operation, the processor 1008 may be configured to execute software stored within the memory 1010, to communicate data to and from the memory 1010, and to generally control operations of the patient support module 1001 pursuant to the software.

The I/O interfaces 1012 may be used to receive user input from and/or for providing system output to one or more devices or components, such as a user device 1020 and/or a second user device 1026. User input may be provided via, for example, a keyboard, mouse, a data/information communication interface, and/or the like. The I/O interfaces 1012 may include, for example, a serial port, a parallel port, a Small Computer System Interface (SCSI), an IR interface, an RF interface, and/or a universal serial bus (USB) interface.

A network interface 1014 may be used to transmit and receive data/information from the patient support module 1001. The network interface 1014 may include, for example, a 10BaseT Ethernet Adaptor, a 100BaseT Ethernet Adaptor, a LAN PHY Ethernet Adaptor, a Token Ring Adaptor, a wireless network adapter (e.g., WiFi), or any other suitable network interface device. The network interface 1014 may include address, control, and/or data connections to enable appropriate communications.

The memory 1010 (memory system) may include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the memory 1010 may incorporate electronic, magnetic, optical, and/or other types of storage media. In some instances, the memory system 1010 may have a distributed architecture, where various components are situated remote from one another, but may be accessed by the processor 1008.

The memory 1010 may include one or more software programs, each of which comprises an ordered listing of executable instructions for implementing logical functions. For example, the memory 1010 may include the EFG configuration application 606, the patient modeling application 608, the imaging data 610, and a suitable operating system (O/S) 1018. The operating system 1018 may, essentially, control the execution of other computer programs, and provides scheduling, input-output control, file and data management, memory management, and communication control and related services.

The patient support module 1001 may include an image processing module 1016. The image processing module 1016 may processes the image data from the user device 1020 and image data from the second user device 1026. In some instances, the image processing module 1016 may use artificial intelligence and/or machine learning, such as image recognition, to identify the user and/or portion of the user's body (e.g., head, torso, total body, etc.). In some instances, the image processing module 1016 may use one or more object tracking algorithms and/or the like to determine/detect the locations of various tracking points on the user. For example, tracking points may include body locations (e.g., head, bones/ligaments, joints, etc.), and/or facial expression points (e.g., eyes, nose, eyebrows, etc.). The locations of the various tracking points may be provided to an avatar mapping and rendering module 1025. The avatar mapping and rendering module 1025 may use one or more mapping algorithms to map the tracked points of the user to an avatar (e.g., a generic image, a replicated image, a wired/stick image, a virtual image, etc.). Mapping the tracked points of the user to an avatar may enable one or more captured images of the user (e.g., the image data) to be represented by an avatar. The patient support module 1001 (the avatar mapping and rendering module 1025) may send the avatar (e.g., data/information indicative of the avatar, etc.) to the user device 1020 and/or the second user device 1026 for display.

In some instances, to assist the user with transducer array placement, the image processing module 1016 may use facial recognition with the image data to identify the user. The image processing module 1016 may use object recognition with the image data to identify the user (e.g., identify distinguishing marks/scars on the user, etc.) and/or the portion of the user's body (e.g., head, torso, total body, etc.) represented by the image data. In some instances, the image processing module 1016 may use object recognition with the image data to determine "sensitive areas" such as scarred areas, blemished areas, genitalia, and/or the like. The image processing module 1016 may modify the image data to obscure, occlude, and/or the like the "sensitive areas", such as when the image data is displayed.

In some instances, the image processing module 1016 may determine one or more landmarks from the image data. For example, the image processing module 1016 may be used to determine/detect anatomical landmarks from the image data. In one example, the image processing module 1016 may determine one or more landmarks indicated by the image data received from the user device 1020 and determine one or more landmarks indicated by the image data received from the second user device 1026. Furthermore, the image processing module 1016 may determine the one or more landmarks indicated by the image data received from the user device 1020 correspond to the one or more landmarks indicated by the image data received from the second user device 1026. The image processing module 1016 may use artificial intelligence and/or machine learning, such as image/object recognition, to identify one or more landmarks (e.g., anatomical landmarks, artificial landmarks, etc.) depicted by one or more images of the plurality of images included with the image data. In some instances, the image processing module 1016 may use one or more object identification and/or tracking algorithms to determine/detect the locations of the one or more landmarks. In some instances, the image processing module 1016 may use object recognition with the image data to determine "sensitive areas" such as scarred areas, blemished areas, genitalia, and/or the like. The image processing module 1016 may modify the image data to obscure, occlude, and/or the like the "sensitive areas", such as when the image data is displayed.

The image processing module 1016 may be used to determine/detect objects depicted by the image data, such as the actual (e.g., real-time, etc.) placement of one or more transducer arrays on a user and/or a portion of the body of the user.

In some instances, the portion of the user's body may have one or more regions, such as the back of the user's head, that are devoid of landmarks that may be determined/detected by object recognition and used to determine the placement position(s) for the one or more transducer arrays. The image processing module 1016 may use machine learning to predict and/or estimate the placement position(s) for the one or more transducer arrays, for example, in scenarios where one or more portions of the one or more transducer arrays are not present and/or represented within the plurality of images. The image processing module 1016 may include a trained machine learning model that may estimate/predict the complete shape, configuration, and or placement of a transducer array when only one or more portions of the transducer array is present and/or represented within the plurality of images. Estimated shapes, configurations, and/or placement position(s)s of the one or more transducer arrays may be combined with the placement position(s) for the one or more transducer arrays determined from object recognition to determine the complete shape, configuration, and or placement of the one or more transducer arrays. The image processing module 1016 may assign estimated points/coordinates to the estimated shapes, configurations, and/or placement position(s)s of the one or more transducer arrays.

The image processing module 1016 may use estimated shapes, configurations, placement position(s) of the one or more transducer arrays, and/or one or more landmarks as points of reference for coordinate axes for a coordinate system (e.g., 2D coordinate system, 3D coordinate system, world coordinates, etc.). For example, the one or more landmarks may define a position in space (a translation value) that may be used with a transformation and/or a projection matrix to determine 3D points that represent the one or more landmarks in 3D space. A 4×4 matrix may be used to represent the coordinate system (e.g., 2D coordinate system, 3D coordinate system, etc.), and may be used to transform the 3D Points from the coordinate system (e.g., 2D coordinate system, 3D coordinate system, world coordinates, etc.) relative to the second user device 1026 to a coordinate system (e.g., 3D coordinate, etc.) relative to the medical imaging data. For example, the 3D points (e.g., coordinates) may be transformed to and/or associated with 3D coordinates of and/or associated with one or more medical images. The one or more medical images may be received from the user device 1020.

Information/data that identifies the user and/or the portion of the user's body may be sent to the patient support module 1001 (the image processing module 1016) with the image data. Once the user has been identified, the image processing module 1016 may access/obtain a patient model associated with the user, such as the patient model produced by the patient modeling application 608.

The patient support module 1001 may include an image registration module 1017. The image registration may register the image data to a three-dimensional transducer array map (e.g., a patient model combined with a final transducer array layout map, etc.) generated/output by the patient modeling application 608. For example, in some instances, the image registration module 1017 may determine a relationship between a user coordinate system, such as a coordinate system based on a vantage point of the user and/or the user device 1020 (e.g., a vantage point of the imaging module 1021, etc.), a coordinate system of the object (e.g., the user) to which one or more transducer arrays are to be applied, and a coordinate system for the three-dimensional transducer array map. The image registration module 1017 may align, anchor, and/or stabilize the three-dimensional transducer array map relative to the image of the object to which one or more transducer arrays are to be applied based on a center of a field of view associated with the vantage point of the user and/or the user device 1020 and a principle axis relationships between the respective coordinate systems. In some instances, the image registration module 1017 may register the image data to a three-dimensional transducer array map by associating landmarks included with the image data to landmarks indicated on the three-dimensional transducer array map. The landmarks may include physical markers, such as a nose, mouth, ear, arms, and/or the like of the user. The landmarks may be determined by the image processing module 1016, for example by based on object recognition and/or the like, and provided to the image registration module 1017 for image registration. The image registration module 1017 may register the image data to a three-dimensional transducer array map based on an affine transformation method and/or a surface analysis method where one or more surface matching algorithms applied to the rigid surfaces of one or more objects identified within the image data and the three-dimensional transducer array map. For example, a collection of points (e.g., a point set, etc.) may be extracted from the contours in the image data and a collection of points (e.g., a point set, etc.) may be extracted from the contours in the three-dimensional transducer array map. An iterative closest point algorithm and/or a correspondence matching algorithm may be applied to both collections of points. The image registration module 1017 may register the image data to a three-dimensional transducer array map based on any method and/or technique.

In some instances, the three-dimensional transducer array map may include and/or be associated with geometrical and/or dimensional information (e.g., shape, size, etc.) for one or more transducers arrays (and/or transducer array support equipment such as patches, disk, and/or the like) to be placed at positions (optimized positions) on the user based on the three-dimensional transducer array map. The registered image data (e.g., video images registered to a three-dimensional transducer array map, etc.) and the geometrical and/or dimensional information (e.g., shape, size, etc.) for the one or more transducers arrays (and/or transducer array support equipment such as patches, disk, and/or the like) may be provided to a graphics rendering module 1019 that generates graphics guides along with the registered image data. Graphic guides may include representations of the one or more transducers arrays (and/or transducer array support equipment such as patches, disk, and/or the like) indicated at positions (e.g., optimized positions) on the user based on the three-dimensional transducer array map.

The registered image data and associated graphic guides may be provided to an image rendering module 1024. The image rendering module 1024 may use the registered image data and associated graphic guides to generate composite data. The composite data may include the three-dimensional transducer array map (and associated graphic guides) combined (e.g., superimposed, overlaid, etc.) with the image data. In another example, the composite data may include locations/positions where one or more transducer arrays are actually placed, as determined and/or indicated by the 3D coordinates associated with the anatomical coordinate system, and optimized (e.g., recommended, etc.) transducer array placement positions indicated by a 3D transducer array layout map. The second user device 1026 may (in real-time), for example via the interface module 1028, cause display of the composite data. For example, the locations/positions where the one or more transducer arrays are placed may be displayed (e.g., superimposed, overlaid, etc.) with the optimized (e.g., recommended, etc.) transducer array placement positions. In some instances, the locations/positions where the one or more transducer arrays are placed may be displayed (e.g., superimposed, overlaid, etc.) with representations of transducer array patches, disks, and/or the like at the optimized (e.g., recommended, etc.) transducer array placement positions.

Furthermore, the image registration module 1017 may register the 3D coordinates associated with the anatomical coordinate system (e.g., the transformed 3D points from the image data) to the 3D transducer array layout map. For example, the image registration module 1017 may determine coordinates of the various landmarks indicated by image data that have been transformed to the anatomical coordinate system. The image registration module 1017 may determine coordinates of one or more landmarks indicated by the 3D transducer array layout map and/or coordinates of one or more one or more transducer arrays indicated by the 3D transducer array layout map. The image registration module 1017 may determine that the transformed coordinates of the various landmarks indicated by image data (e.g., the transformed 3D points from the image data) correspond to the coordinates of one or more landmarks and/or transducer arrays indicated by the 3D transducer array layout map.

In some instances, the image registration module 1017 may determine a relationship between the anatomical coordinate system (e.g., the transformed 3D points from the image data) and a coordinate system for the 3D transducer array layout map. The image registration module 1017 may align, anchor, and/or stabilize the 3D transducer array layout map relative to the anatomical coordinate system (e.g., the transformed 3D points from the image data) based on a center of a field of view associated with a vantage point and/or view point image included with the image data and a principle axis relationships between the respective coordinate systems. In some instances, the image registration module 1017 may register the 3D coordinates associated with the anatomical coordinate system (e.g., the transformed 3D points from the image data) to the 3D transducer array layout map based on an affine transformation method and/or a surface analysis method where one or more surface matching algorithms applied to the rigid surfaces of one or more objects identified within the image data and the 3D transducer array layout map. For example, a collection of points (e.g., a point set, etc.) may be extracted from the contours in the image data and a collection of points (e.g., a point set, etc.) may be extracted from the contours in the 3D transducer array layout map. An iterative closest point algorithm and/or a correspondence matching algorithm may be applied to both collections of points. The image registration module 1017 may register the 3D coordinates associated with the anatomical coordinate system (e.g., the transformed 3D points from the image data) to the 3D transducer array layout map based on any method and/or technique.

For example, in some instances, the patient support module 1001 (e.g., the image processing module 1016, the image registration module 1017, etc.) may determine one or more landmarks indicated by medical image data associated with a user. A projection matrix may be used to determine a 2D representation of the one or more landmarks indicated by the medical image data. The patient support module 1001 may also determine, for example using object recognition, one or more landmarks indicated by the first image data received from the user device 1020 and one or more landmarks indicated by the second image data received from the second user device 1026. The patient support module 1001 may determine that the 2D representation of the one or more landmarks indicated by the first image data correspond to the one or more landmarks indicated by the second image data. The patient support module 1001 may determine, based on the correspondence between the 2D representation of the one or more landmarks indicated by the first image data and the one or more landmarks indicated by the second image data, a representation of the one or more landmarks indicated by the image data received from the second user device 1026 in three-dimensional (3D) space. The representation of the one or more landmarks indicated by the second image data received from the second user device 1026 in three-dimensional (3D) space may then be associated and/or registered to the 3D transducer array layout map that includes recommended placement positions for transducer arrays.

As described, an avatar may be a generic/replicated representation of the user and/or a portion of the user's body such as a generic image, a replicated image, a wired/stick image, virtual image, and/or the like. The user device 1020, for example via the interface module 1022, and/or the second user device 1026, for example via the interface module 1028, may display the avatar. In some instances, the avatar may be displayed as a static (e.g., non-moving, etc.) image representing the user and/or a portion of the user's body. In some instances, mapping the tracked points of the user to an avatar and one or more kinetic algorithms may be used to cause the avatar to mirror, represent, generalize, and/or the like, movements on the user based on the image data.

Figure 11A:
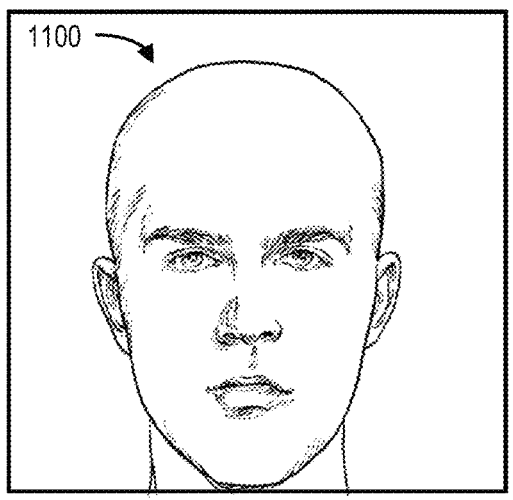
FIGS. 11A and 11B show examples generating a three-dimensional model associated with an image data.
Figure 11B:
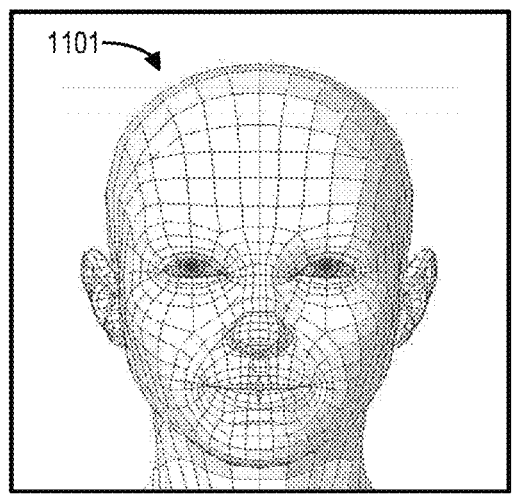

FIG. 11A illustrates an example image data (e.g., video) that is capture by a user device. A video image 1100 of a relevant area for transducer array placement (e.g., the head of the user) user may be captured by one or more cameras and displayed to the user via a user device, for example, in real-time. For example, in some instances, the video image 1100 may include image data captured by a different camera (imaging module) associated with each of one or more user devices. FIG. 11B illustrates an example avatar 1101 that may be used for assisted transducer array placement generated from the video image 1100. The avatar 1101 may be displayed as a static (e.g., non-moving, etc.) avatar representing the user and/or a portion of the user's body. For example, the avatar 1101 represents the head of the user depicted by the video image 1100. In some instances, mapping the tracked points of the user to an avatar and one or more kinetic algorithms may be used to cause the avatar to mirror, represent, generalize, and/or the like, movements on the user based on the image data, such as movements associated with transducer array placement and/or the like.

Figure 12A:
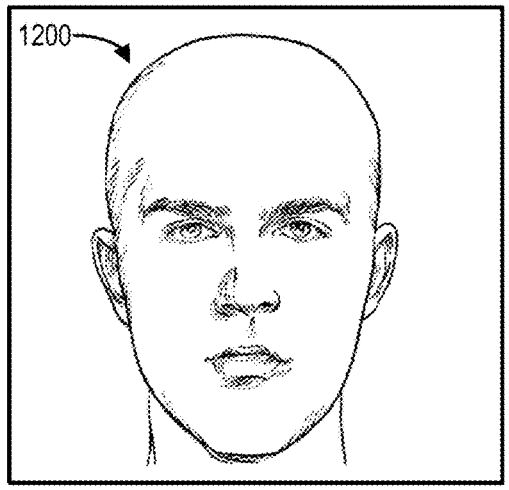
FIGS. 12A-12D show examples generating a composite data associated with an image data.
Figure 12B:
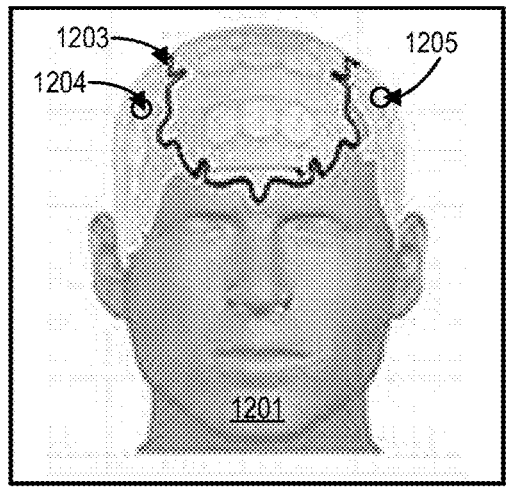

FIG. 12A illustrates example image data (e.g., video) that may be used for assisted transducer array placement. A video image 1200 of a relevant area for transducer array placement on a user (e.g., the head of the user) may be captured by one or more cameras and displayed to the user via a user device, for example, in real-time. FIG. 12B illustrates an example three-dimensional transducer array map 1201 that may be used for assisted transducer array placement. The three-dimensional transducer array map may include one or more graphic guides. Graphic guides may indicate locations where objects associated with TTFields treatment are to be placed/positioned on the user. For example, graphic guide 1203 may be an outline of a transducer array patch placed in a pre-determined position (an optimized position) on the three-dimensional transducer array map 1201 for effective TTfields treatment. Graphic guides 1204 and 1205 may indicate locations where transducers are to be placed on the user for effective TTfields treatment.

Figure 12C:
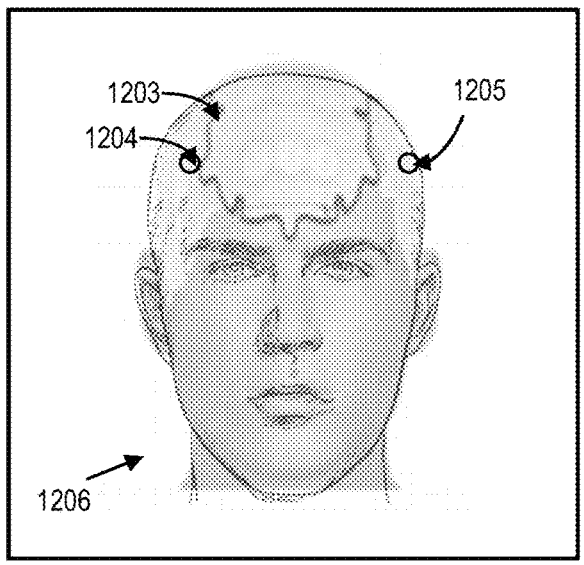

FIG. 12C illustrates an example of composite data 1206 presented in an actual image and/or realistic depiction of the patient/subject and/or the portion of the patient's/subject's body. The composite data 1206 may be displayed to the user via a user device, for example, in real-time, to assist the user transducer array placement. In one example, the composite data comprises the one or more transducer placement positions overlaid on the one or more recommended transducer placement positions. In a more specific example, the composite data comprises a three-dimensional (3D) model that indicates the one or more transducer placement positions and the one or more recommended transducer placement positions.

Figure 12D:
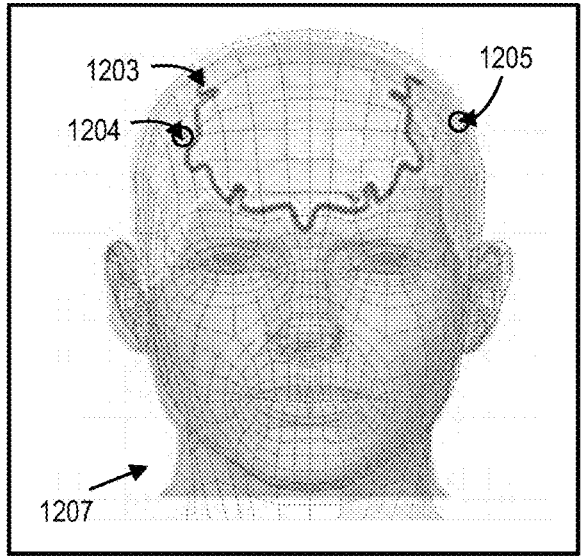

FIG. 12D illustrates another example of composite data 1207 presented in a representative image (e.g., avatar, etc.) of the patient/subject and/or the portion of the patient's/subject's body. The composite data 1207 may be displayed to the user (e.g., via the second user device 1026, etc.), for example, in real-time, to assist the user transducer array placement. The composite data 1207 may include the three-dimensional transducer array map 1201 superimposed/overlaid with the avatar 1101.

Object recognition and tracking (e.g., performed by the image processing module 1016, etc.) may be used to identify objects in image data that are represented by a graphic guide, such as a transducer array, a transducer array patch, and/or a transducer array attachment component (e.g., disk, tape, etc.), and/or the like. For example, object recognition and tracking may be used to track the user's motion as they place (or attempt to place) an object represented by a graphic guide on a portion of the user's body. In some instances, audible (voice) instructions (via the interface module 1028, etc.) may be provider to user to guide the user's motion as they place (or attempt to place) an object represented by a graphic guide on a portion of the user's body. In FIG. 12D, in some instances, movements of the avatar 1101 may mirror movements of the user. For example, movements made by the user when placing a transducer array at one or more positions may be mirrored by the avatar 1101. In some instances, the avatar 1101 and/or composite data 1207 may remain primarily static (non-moving) with only one or more portions of the composite data 1207, such as a represented a transducer array and/or the graphic guides, mirroring/representing the movements of the user, such as the movement of a transducer array when placing the transducer array at one or more positions.

Feedback and/or confirmation may be provided to the user to indicate placement of an object represented by a graphic guide on the user (the skin surface of the user) via the second user device 1026. For example, placement (or an attempted placement) of a transducer array patch at a position on the user indicated by the graphic guide 1203, and/or placement (or an attempted placement) of transducers at positions on the user indicated by the graphic guides 1204 and 1205, may cause an indication to be provided to the user. In some instances, graphic guides may be color coded to indicate placement, on the user, of an object represented by a graphic guide. For example, a graphic guide may be represented in a yellow color. Proper placement of an object represented by the graphic guide may cause the graphic guide to transition to a green color, and improper placement of the object may cause the graphic guide to transition to a red color. In some instances, audible indicators/notifications may be provided to the user to indicate proper and/or improper placement of an object represented by a graphic guide.

Proper and/or improper placement of an object represented by a graphic guide may be based on one or more tolerance thresholds. In some instances, an object represented by a graphic guide that is placed on the user at a position indicated by the graphic guide may be determined, for example by object recognition and correlation of coordinate systems (e.g., the coordinate system of the user, the coordinate system for the three-dimensional transducer array map, etc.), to be within or without a target metric for the position indicated by the graphic guide. In some instances, one or more sensing components, such as accelerometers, gyroscopes, tactile sensors, global positioning sensors, and/or the like, configured with the an object represented by a graphic guide (e.g., a transducer array patch, etc.) may be used to provide data/information that may be used to determine the location/position of the object relative to the graphic guide. The location/position of the object relative to the graphic guide may compared to one or more location/position thresholds to determine proper and/or improper placement of the object.

Figure 13A:
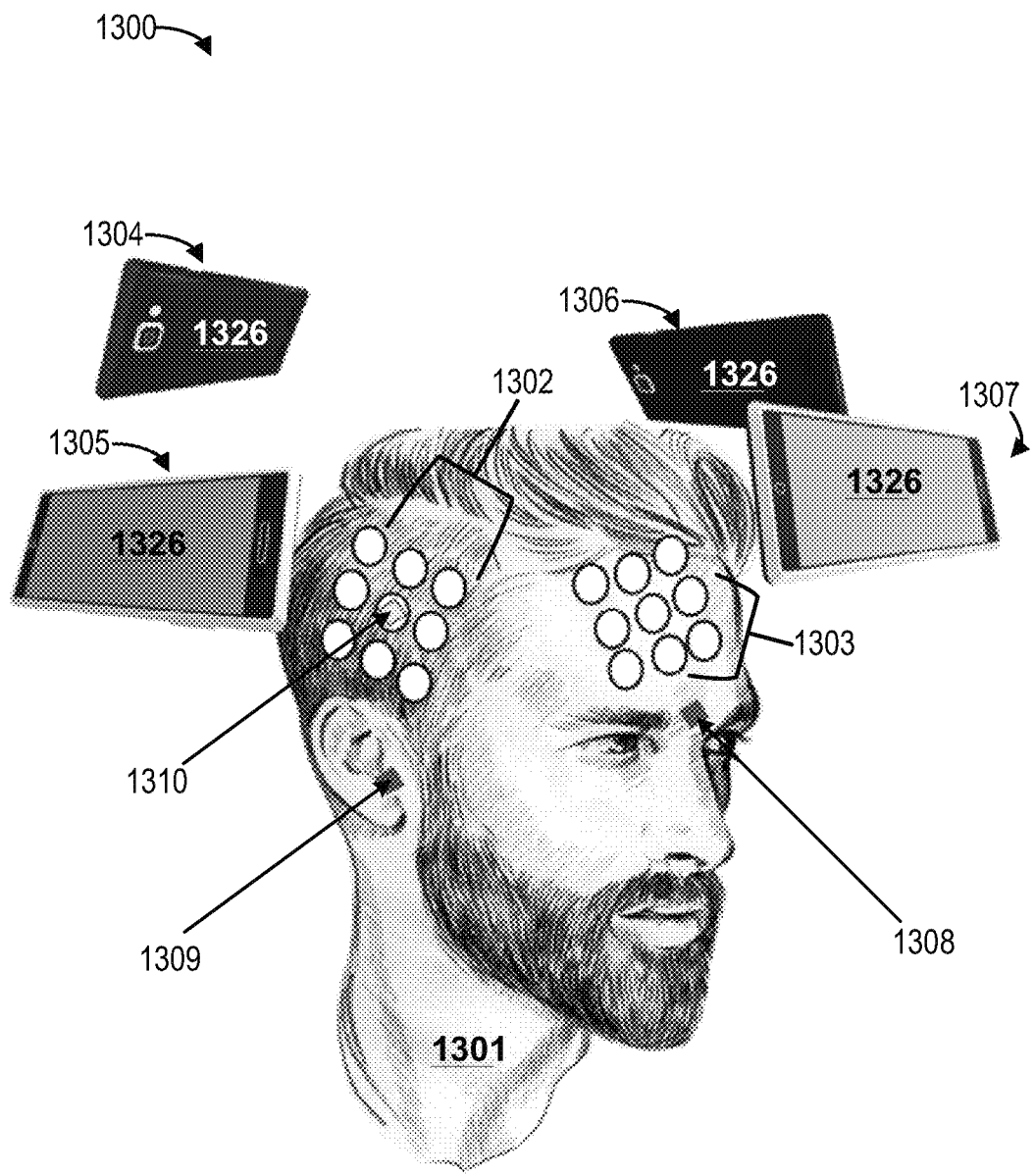
FIGS. 13A-13D show other examples for guided transducer placements for TTFields.

FIGS. 13A-13D show an example for guided transducer placements for TTFields. FIG. 13A shows an example system 1300 for determining and/or capturing image data that may be used for guided transducer array placement. The second user device 1026 may capture a plurality of images of a user 1301, such as images of the user's head and/or any other portion of the user's body where TTFields treatment is to be administered. Transducers arrays may be placed at different positions on the user 1301. For example, transducer arrays 1302 and 1303 may be placed on the head of the user 1301.

To determine whether the transducer arrays 1302 and 1303 are placed at positions that promote optimal efficacy of TTFields treatment, the second user device 1026 may capture a plurality of images of the user 1301 that depict where the transducer arrays 1302 and 1303 are placed relative to the user 1301. The plurality of images may be taken for multiple vantage points, viewpoints, and/or the like. For example, the second user device 1026 may capture images from positions 1304, 1305, 1306, and 1307.

As described, image data associated with and/or indicative of the plurality of images may include data/information (e.g., features, data indicative of one or more recognized objects, coordinate data/information, etc.) extracted from and/or associated with the plurality of images. For example, image data may include data indicative of one or more landmarks and/or tracking points, such as anatomical landmarks and/or visual/artificial landmarks. Anatomical landmarks may include body locations (e.g., head, bones/ligaments, joints, etc.), and/or facial expression points (e.g., eyes, nose, eyebrows, etc.). For example, anatomical landmark 1308 may include the root of the nose of the user 1301, and anatomical landmark 1309 may include the tragus of the ear of the user 1301. Visual/artificial landmarks may include one or more indicators (e.g., stickers, marks/temporary tattoos, objects, etc.) placed at one or more locations/positions on the user and/or a portion of the user's body. For example, landmark 1310 may include an indicator (e.g., a sticker, a mark/temporary tattoo, an object, etc.) placed on the transducer array 1302 so that the transducer array 1302 may be determined/identified from the image data.

The one or more landmarks may be used as reference points for coordinate axes for a coordinate system (e.g., 2D coordinate system, 3D coordinate system, etc.) relative to the second user device 1026. The coordinate system (e.g., 2D coordinate system, 3D coordinate system, etc.) relative to the user device 1026 may be used to generate and/or determine 3D points and/or coordinates that may be associated with additional image data associated with the user 1301, such as medical imaging data. The medical imaging data may include a volumetric and/or three-dimensional (3D) representation of the user 1301 and/or the portion of the user's 1301 body (e.g., head, etc.) used to determine a transducer array layout map. The medical imaging data may include magnetic resonance imaging (MRI) data, x-ray computed tomography (x-ray CT) data, single-photon emission computed tomography (SPECT) image data, positron emission tomography (PET) data, and/or the like associated with the user 1301.

To associate 3D points derived from image data associated with the user with one or more medical images associated with the user, the second user device 1026 may generate and/or determine data/information associated with the image data, such as a device identifier, a user identifier, user information, and/or the like. The device identifier, user identifier, user information, and/or the like may be sent to the patient support module 1001 along with the image data and may be used to determine/identify additional image data associated with the user 1301, such as medical imaging data. 3D points indicative one or more placement positions for one or more transducer arrays, derived from image data associated with the user, may be sent from the user device 1026 to the patient support module 1001. The 3D points indicative one or more placement positions for one or more transducer arrays may be associated with medical imaging data. In some instances, the image data and/or the data/information associated with the image data may be sent to the patient support module 1001. The patient support module 1001 may determine 3D points indicative one or more placement positions for one or more transducer arrays and associate the 3D points with medical imaging data.

In one example, one or more landmarks from the image data may be used as reference points for coordinate axes of a coordinate system (e.g., 2D coordinate system, 3D coordinate system, etc.) relative to the user device 1026. The coordinate system (e.g., 2D coordinate system, 3D coordinate system, etc.) relative to the user device 1026 may be used to generate and/or determine 3D points and/or coordinates. The image processing module 1016 may use estimated shapes, configurations, placement position(s)s of the one or more transducer arrays, and/or one or more landmarks as points of reference for coordinate axes for a coordinate system (e.g., 2D coordinate system, 3D coordinate system, world coordinates, etc.) relative to the second user device 1026.

The one or more landmarks, represented in 3D space, may represent and/or be associated with actual placement position(s) for one or more transducer arrays (e.g., transducer arrays 1302 and 1303, etc.). The actual placement actual placement position(s) for one or more transducer arrays (e.g., transducer arrays 1302 and 1303, etc.) may be compared to optimized transducer array placement positions indicated by a 3D transducer array layout map.

The patient support module 1001 may use data/information associated with the image data (e.g., device identifier, user identifier, user information, coordinate data/information, etc.) to determine a transducer array layout map that includes optimized transducer array placement positions associated with the user. The optimized transducer array placement positions may be determined from on one or more TTFields treatment/therapy simulations performed based on the one or more medical images that are associated with the user. The optimized transducer array placement positions may be recommended to the patient/subject, for example, to promote optimal efficacy of TTFields therapy/treatment. For example, the locations/positions where the one or more transducer arrays are actually placed may be displayed (e.g., superimposed, overlaid, etc.) with the optimized (e.g., recommended, etc.) transducer array placement positions.

Figure 13B:
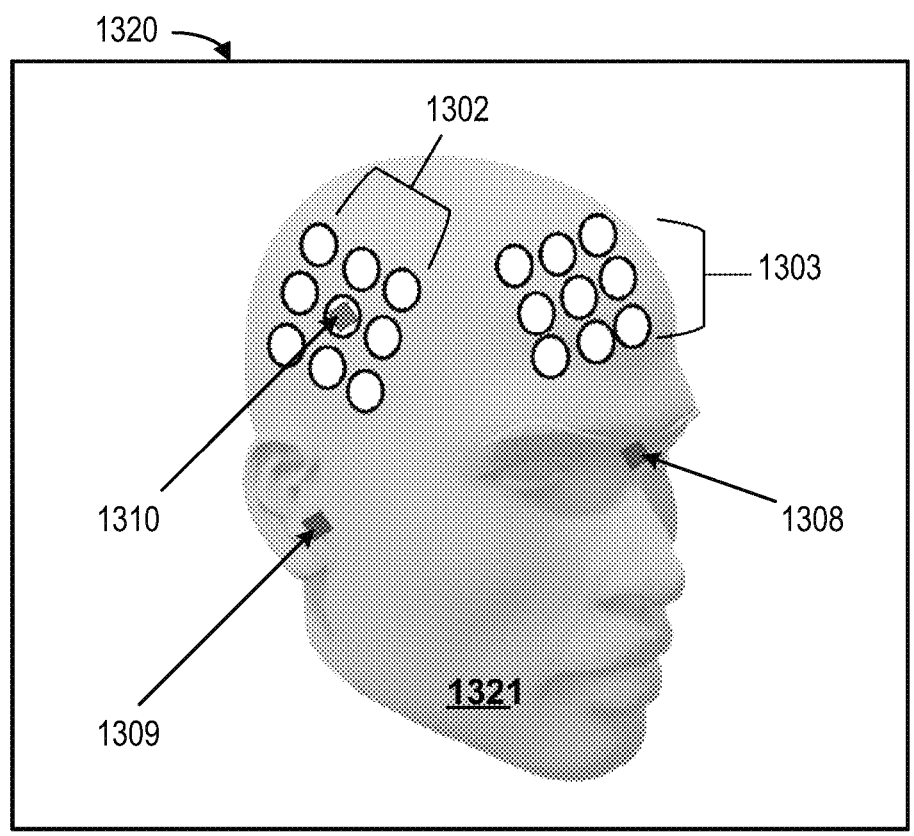

FIG. 13B shows an example representation 1320 of image data used for guiding transducer array placement. Image data determined/captured by the second user device 1026 may be represented as a static (e.g., non-moving, etc.) or dynamic image of the user 1301 of FIG. 13A and/or a portion of the user's body 1301. For example, the avatar 1321 may represent the user 1301. The avatar 1321 may represent the user 1301 to mitigate any privacy concerns and/or user objection associated with communicating image data that depicts "sensitive areas" such as scarred areas, blemished areas, genitalia, and/or the like. As shown, the various landmarks (e.g., the landmark 1310, the anatomical landmarks 1309, etc.), and transducer arrays 1302 and 1103 are represented in the representation 1320.

Figure 13C:
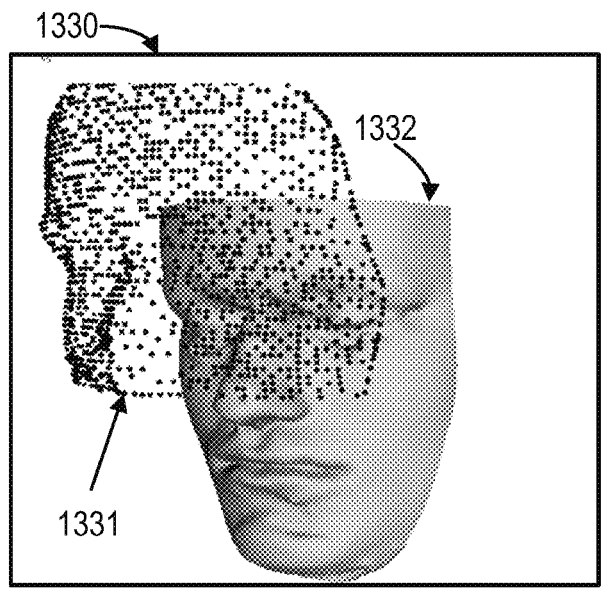
Figure 13D:
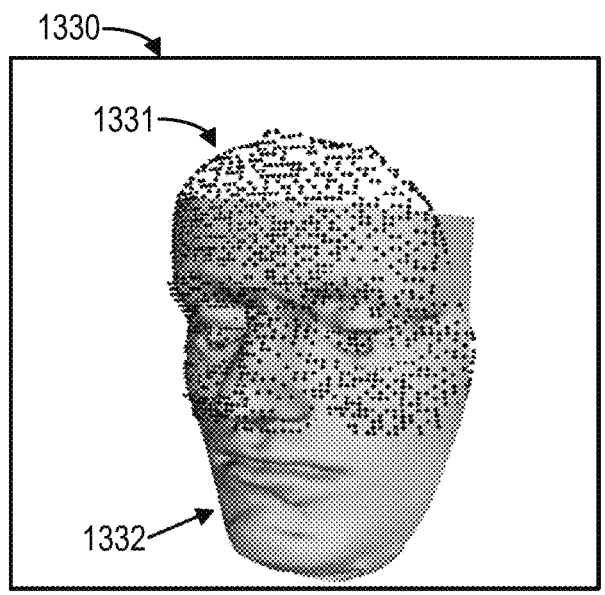

FIGS. 13C and 13D shows an example representation of surface-based registration. The image processing module 1016 may use image data of the user 1301 that depicts a portion of user's body, such as the head, to determine a plurality of points 1331 (e.g., a dataset, etc.) indicative of a facial skin surface of the user 1301. The surface 1332 represents a skin surface extracted from medical image data associated with the user 1301. FIG. 13C shows the initial positions of the plurality of points 1331 determined, for example, by the image processing module 1316. FIG. 13D shows the plurality of points 1331 after they have been registered, for example by the image registration module 1017, to the surface 1332. Registration may be performed, for example, using an iterative closest point algorithm and/or the like.

The patient support module 1001 may determine that the locations/positions where the one or more transducer arrays are actually placed does not match the optimized (e.g., recommended, etc.) transducer array placement positions. For example, based on the comparing the 3D coordinates associated with the anatomical coordinate to the optimized transducer array placement positions indicated by the 3D transducer array layout map, the patient support module 1001 may determine a variance of at least one of the one or more placement positions for one or more transducer arrays from at least one of the optimized (e.g., recommended, etc.) transducer array placement positions.

Figure 14A:
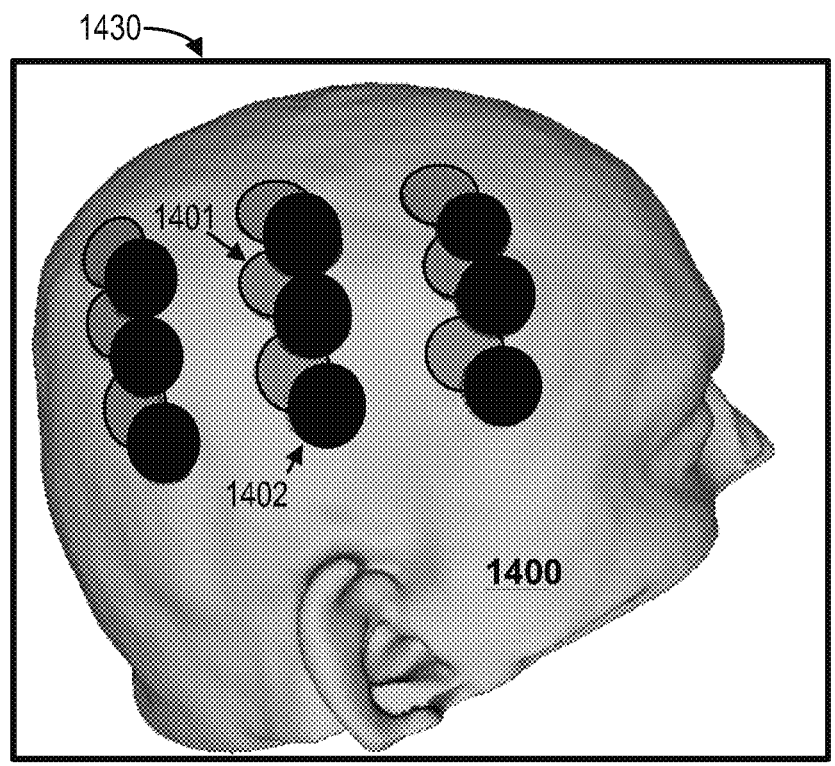
Figure 14B:
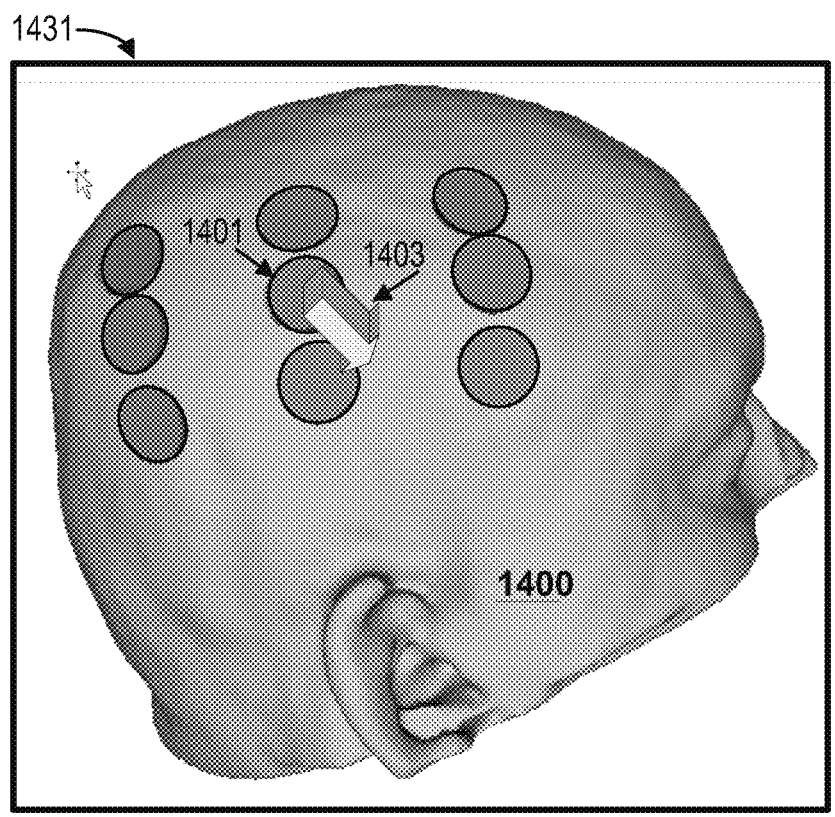

FIGS. 14A-14C depict an example to resolve/correct the variance. FIG. 14A is an example visual notification 1430 that may be used for guiding transducer array placement. Locations/positions where electrodes of a transducer array are placed on a user and optimized (e.g., recommended, etc.) transducer array placement positions may be displayed as a colored mesh on a volumetric representation 1400 of the user and/or portion of the user's body determined from medical imaging data (e.g., MRI data, etc.) associated with the user (e.g., the user 1301, etc.). Locations/positions where electrodes of a transducer array are placed may be represented by gray circles 1401 and optimized (e.g., recommended, etc.) transducer array placement positions may be represented by black circles 1402. The notification may visually instruct the user to lower and pull forward the transducer array when placing it on the surface of the skin so that the locations/positions where the electrodes of the transducer array are placed will match the optimized (e.g., recommended, etc.) transducer array placement positions.

FIG. 14B is an example visual notification 1431 that may be used for guiding transducer array placement. Locations/positions where electrodes of a transducer array are placed on a user and optimized (e.g., recommended, etc.) transducer array placement positions may be displayed on the volumetric representation 1400 of the user and/or portion of the user's body determined from medical imaging data (e.g., MRI data, etc.) associated with the user (e.g., the user 1301, etc.). The locations/positions where electrodes of a transducer array are placed may be represented by the gray circles 1401 any movement of the transducer array required to cause the locations/positions where electrodes of the transducer array to match optimized (e.g., recommended, etc.) transducer array placement positions may be indicated by one or more directional, such as an arrow 1403. The an arrow 1403 may visually instruct the user to lower and pull forward the transducer array when placing it on the surface of the skin so that the locations/positions where the electrodes of the transducer array are placed will match the optimized (e.g., recommended, etc.) transducer array placement positions.

FIG. 14C is an example notification 1432 that may be used for guiding transducer array placement. Any movement of a transducer array required to cause locations/positions where electrodes of the transducer array to match optimized (e.g., recommended, etc.) transducer array placement positions may be indicated by the textual notification 1432. The notification 1432 may inform/instruct the user that the locations/positions where electrodes of a transducer array are placed should be moved in one or more directions. For example, the textual notification 1432 may include instructions related to a transducer array (e.g., TA 2) that indicates "shift 2 cm towards the bottom and 1 cm towards the face." In some instances, the notification 1432 may include additional data/text that encourages the user to follow the instructions included with the notification 1432 presenting/explaining benefits, such as "moving the transducer array 2 cm forward is expected to improve treatment by 10%."

Figure 15:
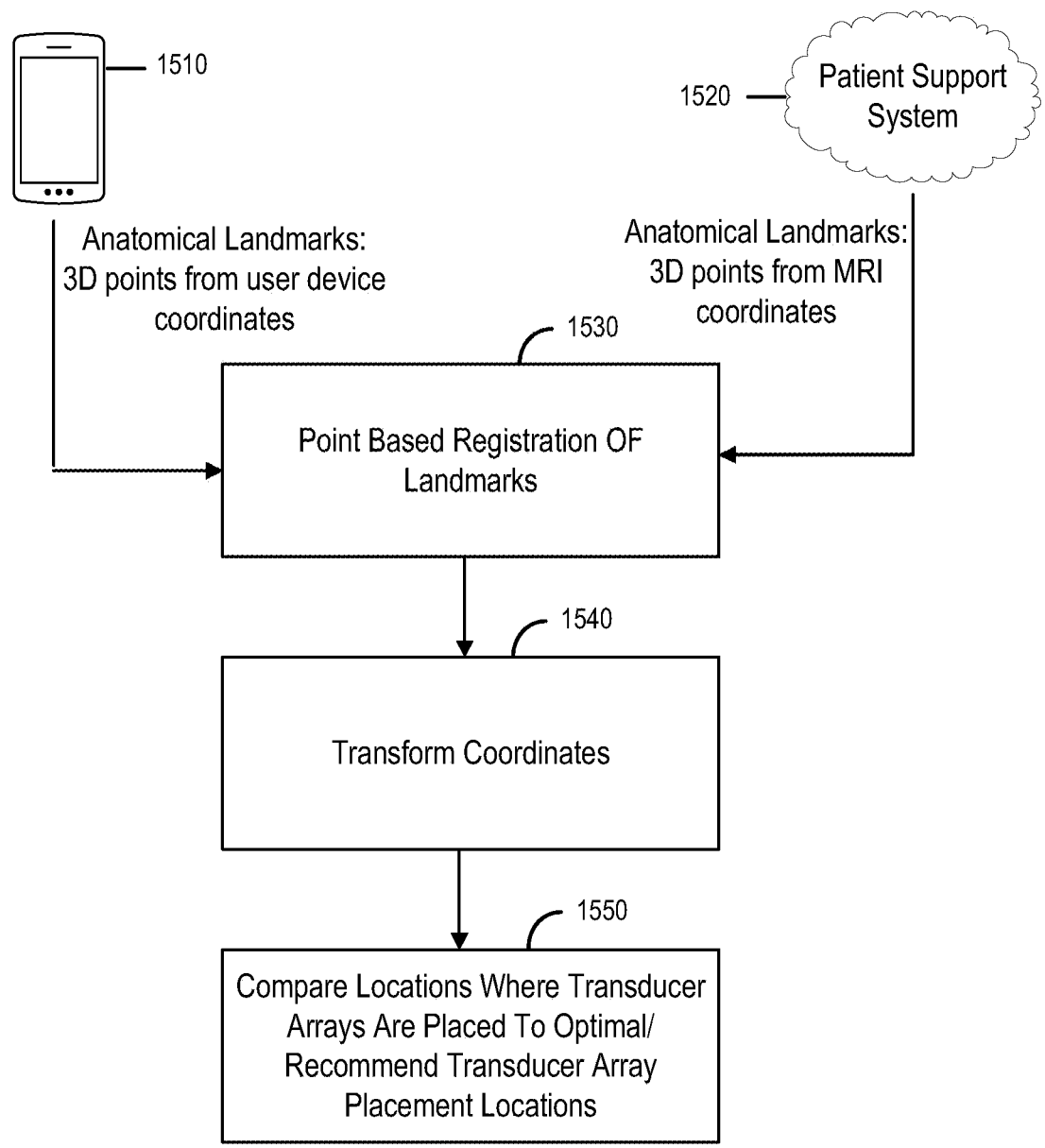
FIG. 15 is a flowchart depicting an example of guided transducer array placements for TTFields.

FIG. 15 is a flowchart of an example method 1500 for guiding transducer array placement. At 1510, a user device (etc., a smartphone, a mobile device, a computing device, etc.) may capture a plurality of images, from different vantage points and/or viewpoints, of a portion of a patient/subject's body where one or more transducer arrays have been placed for TTFields therapy/treatment. The plurality of images may capture the placement position(s) of the one or more transducer arrays.

Points and/or coordinates associated with a coordinate system (e.g., 2D coordinate system, 3D coordinate system, etc.) relative to the plurality of images captured by the user device may be transformed to 3D points and/or coordinates (if they are not already 3D points and/or coordinates). A transformation/projection matrix may be used to transform the points/coordinates of a 2D coordinate system relative to the plurality of images captured by the user device to 3D points/coordinates. For example, object recognition and/or the like may be used to determine/identify one or more anatomical landmarks represented by the plurality of images. Points and/or coordinates associated with the one or more anatomical landmarks may be transformed to 3D points/coordinates. In some instances, the one or more transducer arrays may be used as one or more landmarks and/or may include one or more artificial landmarks. For example, the one or more transducer arrays may include one or more or design attributes (e.g., grooves, indentations, bumps, etc.) that may be used as one or more landmarks (artificial landmarks). Points and/or coordinates associated with the one or more landmarks associated with the one or more transducer arrays may be transformed to 3D points/coordinates. In some instances, the plurality of images may include one or more additional artificial landmarks, such as stickers and/or temporary tattoos placed on the user. Points and/or coordinates associated with the one or more artificial landmarks may be transformed to 3D points/coordinates.

Data/information indicative of the 3D points/coordinates associated with the one or more anatomical landmark derived from the coordinate system relative to the plurality of images captured by the user device may be sent to a computing device and/or patient support system for analysis, such as the patient support module 1001.

Identification information (e.g., a device identifier, a user identifier, user information, etc.) included with the data/information indicative of the 3D points/coordinates associated with the one or more transducer arrays and/or one or more landmarks may also be sent to the computing device and/or system (e.g., the patient support module 1001).

At 1520, the computing device and/or patient support system may use the identification information to determine medical imaging data, such as MRI data, associated with the patient/subject. The MRI data have been used for TTFields therapy/treatment planning for the patient/subject. The MRI data may include a volumetric representation of the portion of a patient/subject's body. The MRI data may include 3D coordinates. Object recognition and/or the like may be used to determine anatomical landmarks within the MRI data that correspond to the anatomical landmarks from the plurality of images. 3D points and/or coordinates associated with anatomical landmarks within the MRI data that correspond to the anatomical landmarks from the plurality of images may be determined.

At 1530, a point-based registration of the anatomical landmarks from the plurality of images and the corresponding anatomical landmarks within the MRI data may be performed. Any method may be used to register the 3D points and/or coordinates associated with the anatomical landmarks from the plurality of images to the 3D points and/or coordinates associated with anatomical landmarks within the MRI.

At 1540, once the 3D points and/or coordinates associated with the anatomical landmarks from the plurality of images to the 3D points and/or coordinates associated with anatomical landmarks within the MRI have been registered, all coordinates associated with the coordinate system relative to the plurality of images captured by the user device may be transformed to the coordinates of the MRI data. As such, any object included within the plurality of images, such as the one or more transducer arrays, may be represented along with the volumetric representation of the portion of a patient/subject's body. Coordinates indicative of locations/positions where the one or more transducer arrays are placed may be used to represent the one or more transducer arrays along with the volumetric representation of the portion of a patient/subject's body. Coordinates indicative of the optimized (e.g., recommended, etc.) transducer array placement positions determined from previous analysis of the MRI data may be used to represent the optimized (e.g., recommended, etc.) transducer array placement positions along with the volumetric representation of the portion of a patient/subject's body.

At 1550, the locations/positions where the one or more transducer arrays are placed may be compared to the optimized (e.g., recommended, etc.) transducer array placement positions. For example, the locations/positions where the one or more transducer arrays are placed may be displayed (e.g., superimposed, overlaid, etc.) with the optimized (e.g., recommended, etc.) transducer array placement positions. In some instances, the locations/positions where the one or more transducer arrays are placed may be displayed (e.g., superimposed, overlaid, etc.) with representations of transducer array patches, disks, and/or the like at the optimized (e.g., recommended, etc.) transducer array placement positions.

FIG. 16 is a flowchart depicting another example of guided transducer array placement for TTFields. At 1620, determining image data, a transducer array map is determined. At 1620, image data (e.g., video data, static/still images, dynamic/interactive images, etc.) associated with a portion of a subject's body is determined. A subject (user) may use one or more cameras to take video images of a portion of the subject's body, such as a video images of the subject's head, torso, and/or the like. In some instances, the method 1600 may include determining, based on the image data, an avatar. The avatar may be a representation of one or more of the subject's body, or the portion of the subject's body. In some instances, the avatar may be a static representation of the one or more of the subject's body, or the portion of the subject's body. In some instances, the avatar may be one or more of a dynamic (e.g., moving, mirrored movement, etc.) representation of the subject or the portion of the subject's body.

At 1630, registering the image data to a three-dimensional (3D) model of the portion of the subject's body, wherein the 3D model comprises one or more positions indicated by the transducer array map. In some instances, registering the image data to the 3D model may cause corresponding portions of the avatar that represent the image data to be registered to the 3D model.

At 1640, generating composite data comprising the image data and one or more representations of transducers arrays associated with the one or more positions indicated by the transducer array map. In some instances, the composite data may comprise the avatar and the one or more representations of transducers arrays associated with the one or more positions indicated by the transducer array map.

The composite data may comprise the one or more representations of the transducers arrays associated with the one or more positions indicated by the transducer array map overlaid on a video image (or the avatar), such as a video image of the portion of the subject's body. In some instances, the method 1600 may include causing display of the composite data.

In some instances, the method 1600 may include determining that a position of one or more transducer arrays and the one or more positions indicated by the transducer array map satisfy a tolerance threshold. Determining that the position of the one or more transducer arrays and the one or more positions indicated by the transducer array map satisfy the tolerance threshold may be based on one or more of object recognition or object tracking. In some instances, the method 1600 may include sending, based on the satisfied tolerance threshold, a notification that indicates that the position of the one or more transducer arrays and the one or more positions indicated by the transducer array map are aligned (e.g., satisfied tolerance threshold, etc.) and/or that the one or more transducer arrays are correctly (e.g., accurately, effectively, etc.) placed on the subject. The notification may be an audible notification (e.g., a beep, a chirp, or any other sound, etc.) and/or a visual notification (e.g., displayed on a display with the composite data, etc.). In some instances, the method 1600 may include causing, based on the satisfied tolerance threshold, a change in a color of the one or more representations of transducers arrays. The change in the color may indicate that the position of the one or more transducer arrays and the one or more positions indicated by the transducer array map are aligned (e.g., satisfied tolerance threshold, etc.) and/or that the one or more transducer arrays are correctly (e.g., accurately, effectively, etc.) placed on the subject.

FIG. 17 is a flowchart depicting another example of guided transducer array placement. At 1710, a three-dimensional (3D) model of a portion of the subject's body is determined. At 1720, determining, based on the 3D model, a transducer array map, wherein the transducer array map indicates one or more positions on the 3D model. At 1730, receiving an image of the portion of the subject's body. A subject (user) may use one or more cameras to take images (e.g., video images, static/still images, dynamic/interactive images, etc.) of the portion of the subject's body, such as images of the subject's head, torso, and/or the like.

At 1740, determining that the image corresponds to the 3D model. In some instances, object recognition and/or facial recognition may be used to identify the subject from the image. The identified subject may be associated with a predetermined 3D model. In some instances, determining that the image corresponds to the 3D model may include determining one or more visual landmarks associated with the image, determining one or more visual landmarks associated with the 3D model, and determining that the one or more visual landmarks associated with the image correspond to the one or more visual landmarks associated with the 3D model. Determining that the one or more visual landmarks associated with the image correspond to the one or more visual landmarks associated with the 3D model may include determining that each visual landmark of the one or more visual landmarks associated with the image and a respective visual landmark of the one or more visual landmarks associated with the 3D model satisfy a correlation threshold.

At 1750, generating, based on determining that the image corresponds to the 3D model, a composite image comprising the image, the 3D model, and one or more images of transducers arrays associated with the one or more positions. In some instances, the method 1600 may include causing display of the composite image.

FIG. 18 is a flowchart depicting another example of guided transducer array placement. At 1810, receiving two-dimensional (2D) image data associated with a portion of a subject's body, wherein the 2D image data indicates one or more placement positions for one or more transducer arrays. Receiving the 2D image data may include receiving the 2D image data from a user device (e.g., a smart device, a mobile device, an image capturing device, the second user device 1026, etc.). The 2D image data may include and/or be derived from a plurality of images, wherein each image of the plurality of images is associated with a different vantage point relative to the portion of the subject's body. The one or more placement positions for the one or more transducer arrays may include one or more actual and/or real-time placement positions for the one or more transducer arrays. In some instances, the image data may include an avatar associated with the portion of the subject's body.

At 1820, determining, based on the 2D image data, a representation of the one or more placement positions for the one or more transducer arrays in three-dimensional (3D) space. Determining the representation of the one or more placement positions for the one or more transducer arrays in 3D space may include: determining one or more landmarks indicated by the 2D image data, determining a representation of the one or more landmarks indicated by the 2D image data in 3D space, determining one or more landmarks indicated by the 3D image data, and determining that the representation of the one or more landmarks indicated by the 2D image data in 3D space correspond to the one or more landmarks indicated by the 3D image data. The one or more landmarks indicated by the 2D image data and the one or more landmarks indicated by the 3D image data may include one or more of: anatomical landmarks or artificial landmarks. The artificial landmarks may include one or more of: stickers, temporary tattoos, or design attributes of the one or more transducer arrays.

Determining the representation of the one or more placement positions for the one or more transducer arrays in 3D space may include: determining a plurality of coordinates indicated by the 2D image data, wherein the plurality of coordinates represent a surface associated with the portion of the subject's body, determining, based on the plurality of coordinates, a representation of the surface in 3D space, and determining that representation of the surface in 3D space corresponds a surface indicated by the 3D image data.

Determining the representation of the one or more placement positions for the one or more transducer arrays in 3D space may include: determining one or more landmarks indicated by the 3D image data; determining a 2D representation of the one or more landmarks indicated by the 3D image data, determining one or more landmarks indicated by the 2D image data, determining that the 2D representation of the one or more landmarks indicated by the 3D image data correspond to the one or more landmarks indicated by the 2D image data, and determining, based on the correspondence between the 2D representation of the one or more landmarks indicated by the 3D image data and the one or more landmarks indicated by the 2D image data, the representation of the one or more placement positions for the one or more transducer arrays in three-dimensional (3D) space. Determining the representation of the one or more placement positions for the one or more transducer arrays in 3D space may include applying a projection matrix to one or more 2D coordinates associated with the one or more placement positions for the one or more transducer arrays. Determining the 2D representation of the one or more landmarks indicated by the 3D image data may include applying a projection matrix to one or more 3D coordinates associated with the one or more landmarks indicated by the 3D image data.

At 1830, comparing the representation of the one or more placement positions for the one or more transducer arrays in 3D space to one or more recommended placement positions for one or more transducer arrays indicated by 3D image data. Comparing the representation of the one or more placement positions for the one or more transducer arrays in 3D space to the one or more recommended placement positions for the one or more transducer arrays indicated by the 3D image data may include causing display of the representation of the one or more placement positions for the one or more transducer arrays in 3D space overlaid with the one or more recommended placement positions for the one or more transducer arrays indicated by the 3D image data.

At 1840, determining, based on the comparison of the representation of the one or more placement positions for the one or more transducer arrays in 3D space to the one or more recommended placement positions for the one or more transducer arrays indicated by the 3D image data, a variance of at least one of the one or more placement positions for the one or more transducer arrays from at least one of the one or more recommended placement positions for one or more transducer arrays. In some instances, the method 1800 may include sending, based on the variance, a notification. The notification may include one or more instructions for correcting the variance. Correcting the variance may include associating, based on coordinates associated with the one or more placement positions for the one or more transducer arrays in 3D space, new coordinates associated with the one or more placement positions for the one or more transducer arrays in 3D space with coordinates associated with the one or more recommended placement positions for the one or more transducer arrays indicated by the 3D image data.

FIG. 19 is a flowchart depicting another example of guided transducer array placement. At 1910, determining, based on one or more images associated with a portion of a subject's body, first image data, wherein the one or more images indicate one or more transducer array placement positions. At 1920, determining second image data associated with the portion of the subject's body, wherein the second image data comprises one or more recommended transducer array placement positions.

At 1930, registering the first image data to the second image data. Registering the first image data to the second image data may include: determining one or more visual landmarks indicated by the first image data, determining one or more visual landmarks indicated by the second image data, and determining that the one or more visual landmarks indicated by the first image data correspond to the one or more visual landmarks indicated by the second image data.

Determining that the one or more visual landmarks associated with the first image data correspond to the one or more visual landmarks associated with the second image data comprises determining that each visual landmark of the one or more visual landmarks associated with the first image data and a respective visual landmark of the one or more visual landmarks associated with the second image data satisfy a correlation threshold.

At 1940, generating composite data comprising the one or more transducer array placement positions and the one or more recommended transducer array placement positions. The composite data may include a three-dimensional (3D) model that indicates the one or more transducer array placement positions and the one or more recommended transducer array placement positions. The composite data may include the one or more transducer array placement positions overlaid on the one or more recommended transducer array placement positions. In some instances, the method 1900 may include display the composite data.

FIG. 20 is a flowchart depicting another example of guided transducer array placement. At 2010, receiving two-dimensional (2D) image data associated with a portion of a subject's body, wherein the 2D image data indicates one or more placement positions for one or more transducer arrays. Receiving the 2D image data may include receiving the 2D image data from a user device (e.g., a smart device, a mobile device, an image capturing device, the user device 1020, the second user device 1026, etc.). The 2D image data may include and/or be derived from a plurality of images, wherein each image of the plurality of images is associated with a different vantage point relative to the portion of the subject's body. The one or more placement positions for the one or more transducer arrays may include one or more actual and/or real-time placement positions for the one or more transducer arrays. In some instances, the image data may include an avatar associated with the portion of the subject's body.

At 2020, determining, based on the 2D image data, one or more three-dimensional (3D) coordinates that represent the one or more placement positions for one or more transducer arrays. determining the one or more three-dimensional (3D) coordinates may include applying a transformation/projection matrix to one or more points/coordinates associated with the 2D image data.

At 2030, determining, based on the registered 3D coordinates and the 3D image data, a representation of the one or more placement positions for the one or more transducer arrays in 3D space. At 2040, comparing the representation of the one or more placement positions for the one or more transducer arrays in 3D space to one or more recommended placement positions for one or more transducer arrays represented in 3D space. At 2050, determining, based on the comparison of the one or more placement positions for the one or more transducer arrays in 3D space to the one or more recommended placement positions for the one or more transducer arrays represented in 3D space, a variance of at least one of the one or more placement positions for the one or more transducer arrays from at least one of the one or more recommended placement positions for the one or more transducer arrays.

FIG. 21 is a flowchart depicting an example of generating variance data. At 2110, determining, a variance between at least one of one or more placement positions for one or more transducer arrays on a portion of a subject's body indicated by two-dimensional (2D) image data from at least one of one or more recommended placement positions for one or more transducer arrays indicated by three-dimensional (3D) image data.

At 2120, generating variance data, wherein the variance data indicates the variance. In some instances, the variance data may include a 3D representation of the portion of the subject's body, wherein the 3D representation comprises the one or more placement positions for the one or more transducer arrays in 3D space overlaid with the one or more recommended placement positions for the one or more transducer arrays. In some instances, the variance data may include one or more images of the portion of the subject's body that indicate: the one or more placement positions for the one or more transducer arrays and the one or more recommended placement positions for the one or more transducer arrays. In some instances, the variance data may include real-time video data overlaid with a representation of the one or more recommended placement positions for the one or more transducer arrays. The variance data may include one or more instructions for correcting the variance. At 2130, sending, to a user device, the variance data. The user device may display the variance data.

Illustrative Embodiment 1. An apparatus of assisting transducer placements on a subject's body for applying tumor treating fields, the apparatus comprising: one or more processors; and a memory storing processor executable instructions that, when executed by the one or more processors, cause the apparatus to: determine, based on one or more images associated with a portion of a subject's body, a first image data, wherein the first image data comprises one or more transducer placement positions; determine, based on the one or more images, a second image data, wherein the second image data comprises one or more recommended transducer placement positions; register the first image data to the second image data; and generate a composite data comprising the one or more transducer placement positions and the one or more recommended transducer placement positions.

Illustrative Embodiment 2. The apparatus of Illustrative Embodiment 1, wherein the processor executable instructions, when executed by the one or more processors, further cause the apparatus to display the composite data.

Illustrative Embodiment 3. The apparatus of Illustrative Embodiment 1, wherein the processor executable instructions that, when executed by the one or more processors, cause the apparatus to register the first image data to the second image data further cause the apparatus to: determine one or more visual landmarks indicated by the first image data; determine one or more visual landmarks indicated by the second image data; and determine that the one or more visual landmarks indicated by the first image data correspond to the one or more visual landmarks indicated by the second image data.

Illustrative Embodiment 4. The apparatus of Illustrative Embodiment 1, wherein the composite data comprises a three-dimensional (3D) model that indicates the one or more transducer placement positions and the one or more recommended transducer placement positions, and wherein the composite data comprises a variance of at least one of the one or more transducer placement positions from at least one of the one or more recommended transducer placement positions indicated in the 3D model.

Illustrative Embodiment 5. The apparatus of Illustrative Embodiment 4, wherein the processor executable instructions, when executed by the one or more processors, further cause the apparatus to send a notification to a user device of the variance, wherein the notification comprises one or more instructions for correcting the variance.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of assisting transducer placements on a subject's body for applying tumor treating fields, the method comprising:
   receiving one or more images of a portion of a subject's body;
   determining, by one or more processors and based on the one or more images, a first image data, wherein the first image data comprises one or more pairs of transducer placement positions corresponding to locations of one or more pairs of transducers on the subject's body for applying tumor treating fields to the subject's body, wherein the first image data comprises two-dimensional (2D) image data;
   determining, based on one or more medical images associated with the portion of the subject's body, a second image data, wherein the second image data comprises one or more recommended pairs of transducer placement positions, wherein the second image data comprises three-dimensional (3D) image data;
   obtaining, by the one or more processors, a registered image data by registering the 2D image data of the first image data to the 3D image data of the second image data; and
   generating a composite data based on the registered image data, the composite data comprising a 3D model that indicates the one or more pairs of transducer placement positions and the one or more recommended pairs of transducer placement positions.

2. The method of claim 1, wherein the composite data comprises the one or more pairs of transducer placement positions overlaid on the one or more recommended pairs of transducer placement positions.

3. The method of claim 1, further comprising:
   displaying the composite data comprising the 3D model that indicates the one or more pairs of transducer placement positions and the one or more recommended pairs of transducer placement positions at a user device.

4. The method of claim 1, wherein the one or more images comprise a plurality of video data, a plurality of images, an avatar, or a combination thereof.

5. The method of claim 1, wherein registering the first image data to the second image data comprises:
   determining one or more visual landmarks indicated by the first image data;
   determining one or more visual landmarks indicated by the second image data; and
   determining the one or more visual landmarks indicated by the first image data correspond to the one or more visual landmarks indicated by the second image data.

6. The method of claim 5, wherein the one or more landmarks comprise at least one of anatomical landmarks or artificial landmarks.

7. The method of claim 6, wherein the artificial landmarks comprise at least one of stickers, temporary tattoos, or design attributes of the one or more transducers.

8. The method of claim 1, further comprising:
   determining and outputting, based on the composite data, a variance of at least one of the one or more pairs of transducer placement positions from at least one of the one or more recommended pairs of transducer placement positions.

9. The method of claim 8, further comprising:
   sending a notification regarding the variance to a user device, wherein the notification comprises one or more instructions for correcting the variance.

10. The method of claim 1, wherein the one or more pairs of transducer placement positions indicated by the first image data comprise one or more real-time placement positions for the one or more pairs of transducers.

11. The method of claim 1, wherein the composite data is generated based on the registered image data and associated graphic guides, wherein the associated graphic guides comprise representations of one or more pairs of transducers based on a three-dimensional transducer map.

12. The method of claim 1, wherein the one or more medical images associated with the portion of the subject's body are obtained using at least one of magnetic resonance imaging, x-ray computed tomography imaging, single-photon emission computed tomography imaging, positron emission tomography imaging.

13. The method of claim 1, wherein the registering comprises transforming coordinates for one or more landmarks in the 2D image data to coordinates of the 3D image data.

14. The method of claim 1, wherein the registering comprises using one of an affine transformation, a surface analysis, or a projection matrix to register the 2D image data of the first image data to the 3D image data of the second image data.

15. An apparatus of assisting transducer placements on a subject's body for applying tumor treating fields, the apparatus comprising:
   one or more processors; and
   a memory storing processor executable instructions that, when executed by the one or more processors, cause the apparatus to:
      receive one or more images of a portion of a subject's body;
      determine, by one or more processors and based on the one or more images, a first image data, wherein the first image data comprises one or more pairs of transducer placement positions corresponding to locations of one or more pairs of transducers on the subject's body for applying tumor treating fields to the subject's body, wherein the first image data comprises two-dimensional (2D) image data;
determine, based on one or more medical images associated with the portion of the subject's body, a second image data, wherein the second image data comprises one or more recommended pairs of transducer placement positions, wherein the second image data comprises three-dimensional (3D) image data;
obtain, by the one or more processors, a registered image data by registering the 2D image data of the first image data to the 3D image data of the second image data; and
generate a composite data based on the registered image data, the composite data comprising a 3D model that indicates the one or more pairs of transducer placement positions and the one or more recommended pairs of transducer placement positions.

16. The apparatus of claim 15, wherein the processor executable instructions, when executed by the one or more processors, further cause the apparatus to display the composite data.

17. The apparatus of claim 15, wherein the processor executable instructions that, when executed by the one or more processors, cause the apparatus to register the first image data to the second image data further cause the apparatus to:
determine one or more visual landmarks indicated by the first image data;
determine one or more visual landmarks indicated by the second image data; and
determine that the one or more visual landmarks indicated by the first image data correspond to the one or more visual landmarks indicated by the second image data.

18. The apparatus of claim 15, wherein the composite data comprises a variance of at least one of the one or more pairs of transducer placement positions from at least one of the one or more recommended pairs of transducer placement positions indicated in the 3D model.

19. The apparatus of claim 18, wherein the processor executable instructions, when executed by the one or more processors, further cause the apparatus to send a notification to a user device of the variance, wherein the notification comprises one or more instructions for correcting the variance.

* * * * *